(12) United States Patent
Koontz et al.

(10) Patent No.: US 10,940,226 B2
(45) Date of Patent: Mar. 9, 2021

(54) DISPENSER

(71) Applicant: S. C. Johnson & Son, Inc., Racine, WI (US)

(72) Inventors: Chris A. Koontz, Racine, WI (US); Alex Mecker, Milwaukee, WI (US); Jason K. Stanbro, Sturtevant, WI (US); Gregory G. Pieper, Spring Grove, IL (US); Kevin Harrity, Oak Creek, WI (US); Nathan R. Westphal, Union Grove, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 514 days.

(21) Appl. No.: 15/234,837

(22) Filed: Aug. 11, 2016

(65) Prior Publication Data
US 2017/0252476 A1    Sep. 7, 2017

Related U.S. Application Data

(60) Provisional application No. 62/301,997, filed on Mar. 1, 2016.

(51) Int. Cl.
| | |
|---|---|
| *A61L 9/03* | (2006.01) |
| *A01M 1/20* | (2006.01) |
| *B60H 3/00* | (2006.01) |
| *H05B 3/12* | (2006.01) |
| *B05B 3/18* | (2006.01) |

(Continued)

(52) U.S. Cl.
CPC ........... *A61L 9/037* (2013.01); *A01M 1/2077* (2013.01); *A61L 9/03* (2013.01); *B60H 3/0007* (2013.01); *H05B 3/12* (2013.01); *H05B 3/18* (2013.01); *A61L 9/012* (2013.01); *A61L 9/035* (2013.01);
(Continued)

(58) Field of Classification Search
CPC ...................... A01M 1/2077; A61L 2209/133; A61L 9/012; A61L 9/03; A61L 9/035; A61L 9/037; B60H 2003/005; B60H 3/0007; H05B 2203/021; H05B 3/12; H05B 3/18
USPC ....... 392/395, 403, 136, 390, 391, 392, 393, 392/394, 405; 424/409, 405, 421, 764,
(Continued)

(56) References Cited

U.S. PATENT DOCUMENTS

| | | | |
|---|---|---|---|
| 2,786,406 A | 3/1957 | White | |
| 2,898,649 A | 8/1959 | Murray | |

(Continued)

FOREIGN PATENT DOCUMENTS

| | | |
|---|---|---|
| CN | 202173617 U | 3/2012 |
| CN | 103768638 A1 | 5/2014 |

(Continued)

OTHER PUBLICATIONS

International Search Report & Written Opinion, International Application No. PCT/US2017/012862, dated Jun. 26, 2017, 11 pages.

(Continued)

*Primary Examiner* — Dana Ross
*Assistant Examiner* — Ket D Dang
(74) *Attorney, Agent, or Firm* — Quarles & Brady LLP

(57) ABSTRACT

A dispenser includes a housing having a cavity. A container is provided within the cavity and includes a volatile material therein. The dispenser further includes a resistive heating wire. The container is in thermal communication with at least a portion of the resistive heating wire.

21 Claims, 34 Drawing Sheets

(51) Int. Cl.
  *A61L 9/012* (2006.01)
  *H05B 3/18* (2006.01)
(52) U.S. Cl.
  CPC ... *A61L 2209/133* (2013.01); *B60H 2003/005* (2013.01); *H05B 2203/021* (2013.01)
(58) Field of Classification Search
  USPC ...... 424/DIG. 8, DIG. 10; 514/65, 521, 531, 514/919; 422/125, 123, 124
  See application file for complete search history.

(56) References Cited

U.S. PATENT DOCUMENTS

| | | | |
|---|---|---|---|
| 4,383,951 A * | 5/1983 | Palson | A61L 9/122 239/35 |
| 4,574,181 A | 3/1986 | Spector | |
| 4,702,418 A | 10/1987 | Carter et al. | |
| 4,808,347 A | 2/1989 | Dawn | |
| 4,968,456 A | 11/1990 | Muderlak et al. | |
| 5,234,162 A | 8/1993 | Sullivan | |
| 5,342,584 A | 8/1994 | Fritz et al. | |
| 5,373,581 A | 12/1994 | Smith | |
| 5,394,506 A | 2/1995 | Stein et al. | |
| 5,439,100 A | 8/1995 | Gordon et al. | |
| 5,484,086 A | 1/1996 | Pu | |
| 5,605,308 A | 2/1997 | Quan et al. | |
| 5,788,931 A | 8/1998 | Quintana | |
| 5,833,929 A | 11/1998 | Watson et al. | |
| 5,903,710 A | 5/1999 | Weller et al. | |
| 6,021,254 A | 2/2000 | Hunter | |
| 6,085,026 A * | 7/2000 | Hammons | A61L 9/03 219/544 |
| 6,085,027 A | 7/2000 | Sexton | |
| 6,090,349 A | 7/2000 | Hirano | |
| 6,095,153 A * | 8/2000 | Kessler | A24F 47/008 131/194 |
| 6,099,137 A | 8/2000 | McCormack et al. | |
| 6,135,431 A | 10/2000 | Muhmel et al. | |
| 6,197,263 B1 | 3/2001 | Blount | |
| 6,278,840 B1 | 8/2001 | Millan | |
| 6,285,830 B1 | 9/2001 | Millan | |
| 6,354,710 B1 | 3/2002 | Nacouzi | |
| 6,374,044 B1 | 4/2002 | Freidel | |
| 6,413,476 B1 * | 7/2002 | Barnhart | A61L 9/03 422/123 |
| 6,443,434 B1 | 9/2002 | Vieira | |
| 6,446,583 B2 | 9/2002 | Prather | |
| 6,466,739 B2 | 10/2002 | Ambrosi et al. | |
| 6,580,875 B2 | 6/2003 | Rymer | |
| 6,592,828 B2 | 7/2003 | Munoz | |
| 6,644,507 B2 | 11/2003 | Borut et al. | |
| 6,661,967 B2 | 12/2003 | Levine et al. | |
| 6,782,194 B2 | 8/2004 | Schneiderbauer | |
| 6,796,340 B1 | 9/2004 | Ferris et al. | |
| 6,854,717 B2 | 2/2005 | Millan | |
| 6,859,615 B2 | 2/2005 | Yip et al. | |
| 6,862,403 B2 | 3/2005 | Pedrotti et al. | |
| 6,917,754 B2 | 7/2005 | Pedrotti et al. | |
| 6,920,282 B2 | 7/2005 | He et al. | |
| 6,931,202 B2 | 8/2005 | Pedrotti et al. | |
| 6,950,607 B2 | 9/2005 | Yip et al. | |
| 6,957,779 B2 | 10/2005 | Joshi et al. | |
| 6,996,335 B2 | 2/2006 | Zobele | |
| 7,082,259 B2 | 7/2006 | Zobele | |
| 7,141,215 B2 | 11/2006 | Guan et al. | |
| 7,188,780 B2 | 3/2007 | Martens, III | |
| 7,190,888 B2 | 3/2007 | Wolf et al. | |
| 7,209,650 B2 | 4/2007 | Caserta et al. | |
| 7,213,770 B2 | 5/2007 | Martens, III et al. | |
| 7,341,698 B2 | 3/2008 | Pedrotti et al. | |
| 7,350,720 B2 | 4/2008 | Jaworski et al. | |
| 7,389,943 B2 | 6/2008 | Jaworski | |
| 7,441,360 B2 | 10/2008 | Christianson et al. | |
| 7,462,329 B2 | 12/2008 | Weller | |
| 7,469,844 B2 | 12/2008 | Conway et al. | |
| 7,484,716 B2 | 2/2009 | Morie et al. | |
| 7,497,685 B2 | 3/2009 | Kubicek et al. | |
| 7,503,668 B2 | 3/2009 | Porchia et al. | |
| 7,534,406 B2 | 5/2009 | Takemura | |
| 7,544,331 B1 * | 6/2009 | Pettaway | A61L 9/03 422/125 |
| 7,544,332 B2 * | 6/2009 | De Silva | A01M 1/2077 239/53 |
| 7,548,684 B2 | 6/2009 | Berrido et al. | |
| 7,610,118 B2 | 10/2009 | Schramm et al. | |
| 7,651,666 B2 | 1/2010 | Adair et al. | |
| 7,824,627 B2 | 11/2010 | Michaels et al. | |
| 7,931,213 B2 | 4/2011 | Walter et al. | |
| 7,932,482 B2 | 4/2011 | Norwood et al. | |
| 7,938,338 B2 | 5/2011 | Janakat et al. | |
| 7,954,667 B2 | 6/2011 | Furner et al. | |
| 7,962,017 B2 | 6/2011 | Viera | |
| 7,980,486 B2 | 7/2011 | Trent et al. | |
| 8,005,349 B2 | 8/2011 | Franco | |
| 8,061,562 B2 | 11/2011 | Carpenter et al. | |
| 8,062,598 B2 | 11/2011 | Bertassi et al. | |
| 8,091,734 B2 | 1/2012 | Furner et al. | |
| 8,170,405 B2 | 5/2012 | Harris | |
| 8,196,902 B1 | 6/2012 | Pystin | |
| 8,197,761 B2 | 6/2012 | Miller-Larry | |
| 8,342,363 B2 | 1/2013 | Carpenter et al. | |
| 8,342,370 B2 | 1/2013 | Ross et al. | |
| 8,371,310 B2 | 2/2013 | Brenneise | |
| 8,371,740 B2 | 2/2013 | Pestl et al. | |
| 8,412,029 B2 | 4/2013 | Browder et al. | |
| 8,463,114 B2 | 6/2013 | Fabrega | |
| 8,498,524 B2 | 7/2013 | Ruiz et al. | |
| 8,662,480 B1 * | 3/2014 | Irvin | A61L 9/122 261/26 |
| 8,678,233 B2 | 3/2014 | Furner et al. | |
| 8,718,454 B2 | 5/2014 | Caserta et al. | |
| 8,740,107 B2 | 6/2014 | Marchetti et al. | |
| 8,750,694 B1 | 6/2014 | Porretta et al. | |
| 8,765,063 B2 | 7/2014 | Mazzilli | |
| 8,783,510 B2 | 7/2014 | Reynolds et al. | |
| 8,787,739 B2 | 7/2014 | Hsiao | |
| 8,887,954 B2 | 11/2014 | Carpenter et al. | |
| 8,983,277 B2 | 3/2015 | Hsiao | |
| 8,983,278 B2 | 3/2015 | Ruiz et al. | |
| 8,983,279 B2 * | 3/2015 | Adair | A61L 9/037 392/395 |
| 8,999,259 B2 | 4/2015 | King et al. | |
| 9,031,392 B2 | 5/2015 | Hsiao | |
| 9,042,712 B2 | 5/2015 | Irvin et al. | |
| 9,144,621 B1 | 9/2015 | Finlay | |
| 9,259,750 B2 | 2/2016 | Johnson et al. | |
| 9,352,062 B2 | 5/2016 | Klemm et al. | |
| 9,388,994 B2 | 7/2016 | Hidaka et al. | |
| 9,393,337 B2 | 7/2016 | Gruenbacher et al. | |
| 9,399,080 B2 | 7/2016 | Irvin et al. | |
| 9,408,936 B2 | 8/2016 | Esses | |
| 9,522,208 B2 | 12/2016 | Esses | |
| 9,877,510 B2 * | 1/2018 | Henry, Jr. | A24F 47/008 |
| 9,999,250 B2 * | 6/2018 | Minskoff | H05B 3/46 |
| 2002/0176704 A1 | 11/2002 | Roe | |
| 2003/0138241 A1 | 7/2003 | Pedrotti et al. | |
| 2003/0206834 A1 | 11/2003 | Chiao et al. | |
| 2004/0009103 A1 | 1/2004 | Westring | |
| 2004/0190883 A1 * | 9/2004 | Kompara | A61L 9/035 392/390 |
| 2005/0175331 A1 | 8/2005 | Tan et al. | |
| 2005/0220664 A1 | 10/2005 | Hitzler et al. | |
| 2006/0000922 A1 | 1/2006 | Martens | |
| 2006/0032937 A1 | 2/2006 | Caserta | |
| 2006/0193610 A1 | 8/2006 | Han | |
| 2006/0193611 A1 | 8/2006 | Ruiz Ballesteros et al. | |
| 2006/0292110 A1 | 12/2006 | Reinhardt | |
| 2007/0183924 A1 | 8/2007 | Morgan | |
| 2007/0183981 A1 * | 8/2007 | Varanasi | A01M 1/2077 424/40 |
| 2007/0257016 A1 * | 11/2007 | Jin | A01M 1/2077 219/201 |
| 2007/0262166 A1 | 11/2007 | Majerowski | |

(56) References Cited

U.S. PATENT DOCUMENTS

| | | |
|---|---|---|
| 2008/0095522 A1 | 4/2008 | Deflorian et al. |
| 2008/0277495 A1 | 11/2008 | Duru |
| 2009/0041442 A1 | 2/2009 | Rouse, Jr. |
| 2009/0078253 A1 | 3/2009 | Bao |
| 2009/0196587 A1* | 8/2009 | Cheung .................... A61L 9/037 392/394 |
| 2009/0232710 A1 | 9/2009 | Kinsey |
| 2009/0302019 A1 | 12/2009 | Selenski et al. |
| 2010/0010908 A1 | 1/2010 | Pasuplati et al. |
| 2010/0059602 A1 | 3/2010 | Chiou et al. |
| 2010/0178042 A1* | 7/2010 | Neumann ............ A01M 1/2077 392/386 |
| 2010/0193599 A1 | 8/2010 | Bulter et al. |
| 2010/0326280 A1 | 12/2010 | Hicks |
| 2011/0132995 A1 | 6/2011 | Perman |
| 2011/0134628 A1 | 6/2011 | Pestl |
| 2011/0139810 A1 | 6/2011 | Lee |
| 2012/0000989 A1 | 1/2012 | Bordier |
| 2012/0018529 A1 | 1/2012 | Gammon et al. |
| 2012/0201523 A1 | 8/2012 | Tebe Poves et al. |
| 2012/0224995 A1 | 9/2012 | McMinn |
| 2013/0049236 A1 | 2/2013 | Garon et al. |
| 2014/0091487 A1 | 4/2014 | Belongia |
| 2014/0112649 A1* | 4/2014 | Irvin ...................... A61L 9/03 392/390 |
| 2014/0126892 A1 | 5/2014 | Hsiao |
| 2014/0145004 A1* | 5/2014 | Westphal ................ A61L 9/12 239/59 |
| 2014/0193764 A1 | 7/2014 | Pizzini |
| 2014/0209698 A1 | 7/2014 | Olchovy et al. |
| 2014/0209700 A1 | 7/2014 | Olchovy et al. |
| 2014/0261408 A1* | 9/2014 | DePiano .................. H05B 3/44 128/202.21 |
| 2014/0377130 A1 | 12/2014 | Edwards et al. |
| 2015/0258289 A1 | 9/2015 | Henry et al. |
| 2015/0320899 A1 | 11/2015 | Soliz et al. |
| 2016/0015847 A1 | 1/2016 | Irvin et al. |
| 2016/0022855 A1 | 1/2016 | Esses |
| 2016/0022857 A1 | 1/2016 | Esses |
| 2016/0067367 A1 | 3/2016 | Jin et al. |
| 2016/0107186 A1 | 4/2016 | Chao |
| 2016/0152117 A1 | 6/2016 | Backman et al. |
| 2016/0256585 A1 | 9/2016 | Esses |
| 2016/0279278 A1 | 9/2016 | Gruenbacher et al. |
| 2016/0325605 A1 | 11/2016 | Irvin et al. |
| 2016/0331913 A1 | 11/2016 | Bourque |
| 2017/0128608 A1 | 5/2017 | Hsiao |
| 2018/0064839 A1 | 3/2018 | Hsiao |
| 2018/0126022 A1 | 5/2018 | Hsiao |
| 2018/0126025 A1 | 5/2018 | Hsiao |

FOREIGN PATENT DOCUMENTS

| | | |
|---|---|---|
| CN | 105188777 A1 | 12/2015 |
| CN | 204951729 U | 1/2016 |
| DE | 202013101904 U1 | 6/2013 |
| EP | 0511853 A2 | 11/1992 |
| EP | 1175833 A1 | 1/2002 |
| ES | 2255422 A1 | 6/2006 |
| JP | 01060918 U | 4/1989 |
| JP | 04136082 U | 12/1992 |
| JP | 2002200154 A | 7/2002 |
| JP | 2003225293 A | 8/2003 |
| JP | 2004524864 A | 8/2004 |
| JP | 2004313004 A | 11/2004 |
| JP | 2010506577 A | 3/2010 |
| JP | 2010532170 A | 10/2010 |
| JP | 2015531621 A | 11/2015 |
| JP | S56020869 B | 11/2015 |
| KR | 20040043304 A | 5/2004 |
| WO | 1997039778 A1 | 10/1997 |
| WO | 2003077961 A1 | 9/2003 |
| WO | 2004028574 A1 | 4/2004 |
| WO | 2005092399 A1 | 10/2005 |
| WO | 2007018402 A1 | 2/2007 |
| WO | 2007083042 A1 | 7/2007 |
| WO | WO2007142851 A2 | 12/2007 |
| WO | 2011020491 A1 | 2/2011 |
| WO | 2013106982 A1 | 7/2013 |
| WO | 2014022164 A1 | 2/2014 |
| WO | 2014025720 A1 | 2/2014 |
| WO | 2014055478 A1 | 4/2014 |
| WO | 2014087173 A1 | 6/2014 |
| WO | 2015116934 A1 | 8/2015 |
| WO | 2016083165 A1 | 6/2016 |
| WO | 2016096272 A1 | 6/2016 |
| WO | 2016155333 A1 | 10/2016 |
| WO | 2016180663 A1 | 11/2016 |

OTHER PUBLICATIONS

International Search Report & Written Opinion, International Application No. PCT/US2017/012727, dated Dec. 5, 2017, 29 pages.

Non Final Office Action, U.S. Appl. No. 15/005,651 dated Nov. 3, 2017, 11 pages.

International Search Report & Written Opinion, International Application No. PCT/US2017/018130, dated Jun. 2, 2017, 16 pages.

Grounds for Rejection issued in Chinese Application No. 201780027275.6, dated Apr. 29, 2020, 11 pages.

First Office Action from corresponding Japanese Patent Application No. 2018-538830, dated Dec. 1, 2020 (6 pages).

First Office Action from corresponding Chinese Patent Application No. 201780019773.6, dated Nov. 12, 2020 (9 pages) (English translation unavailable).

* cited by examiner

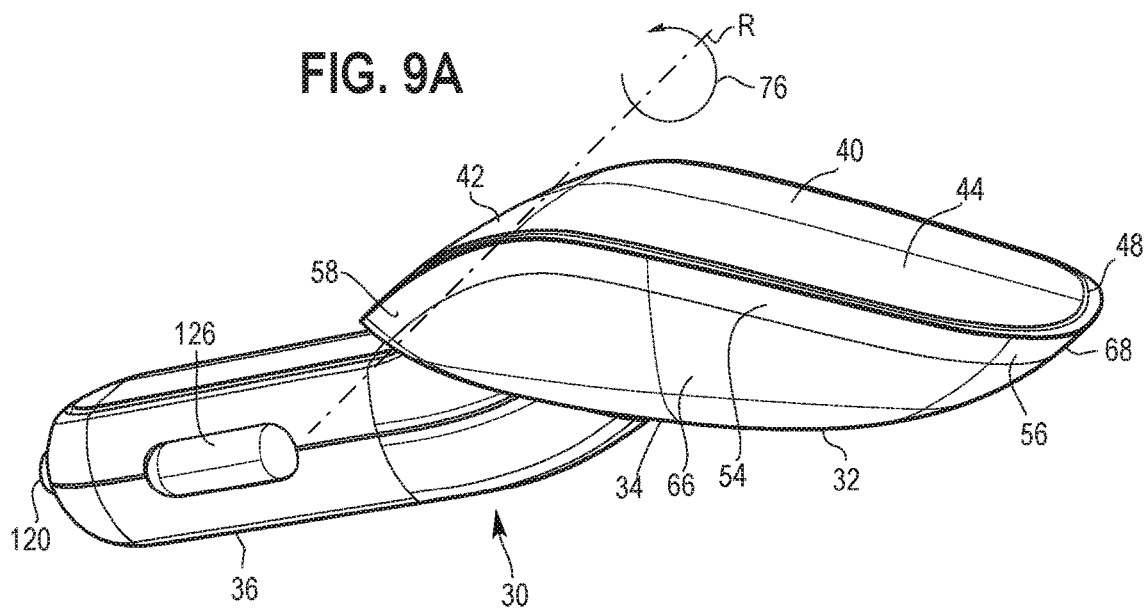
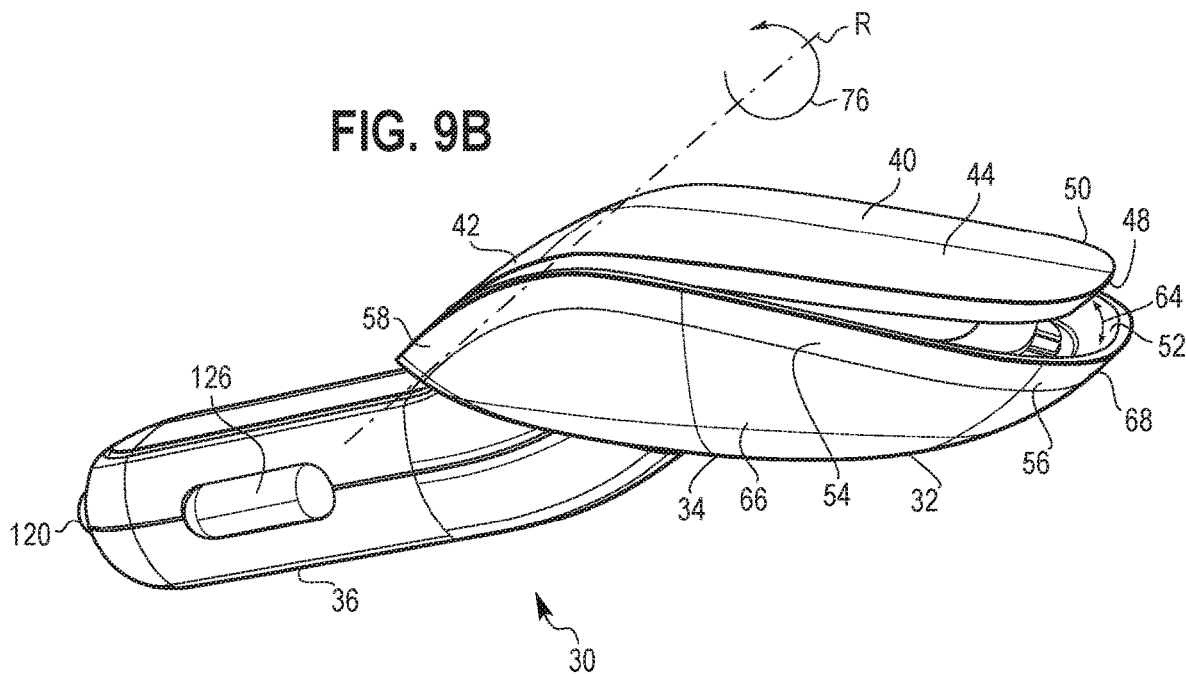

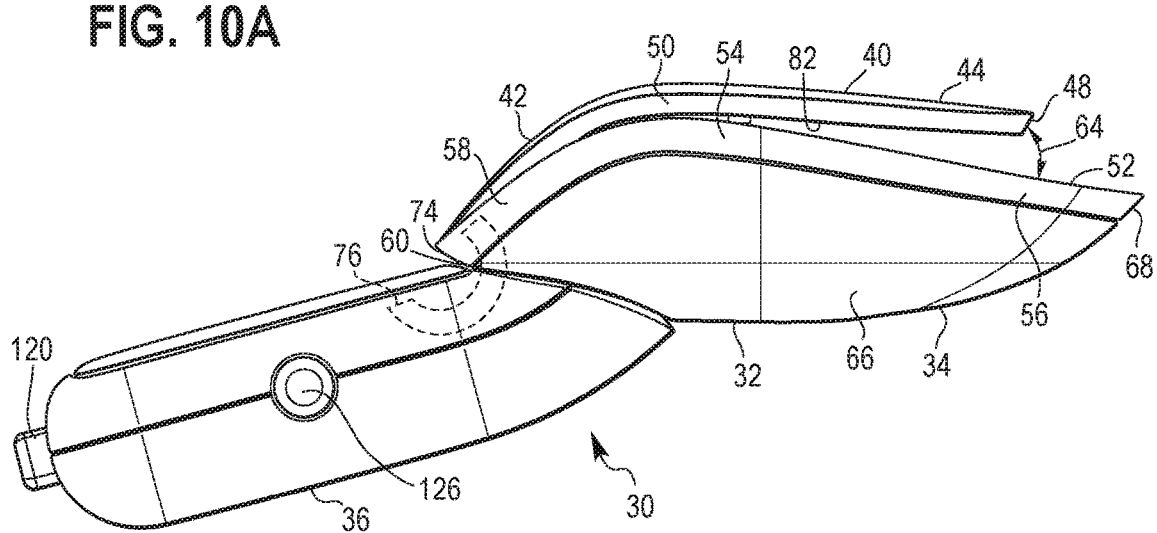
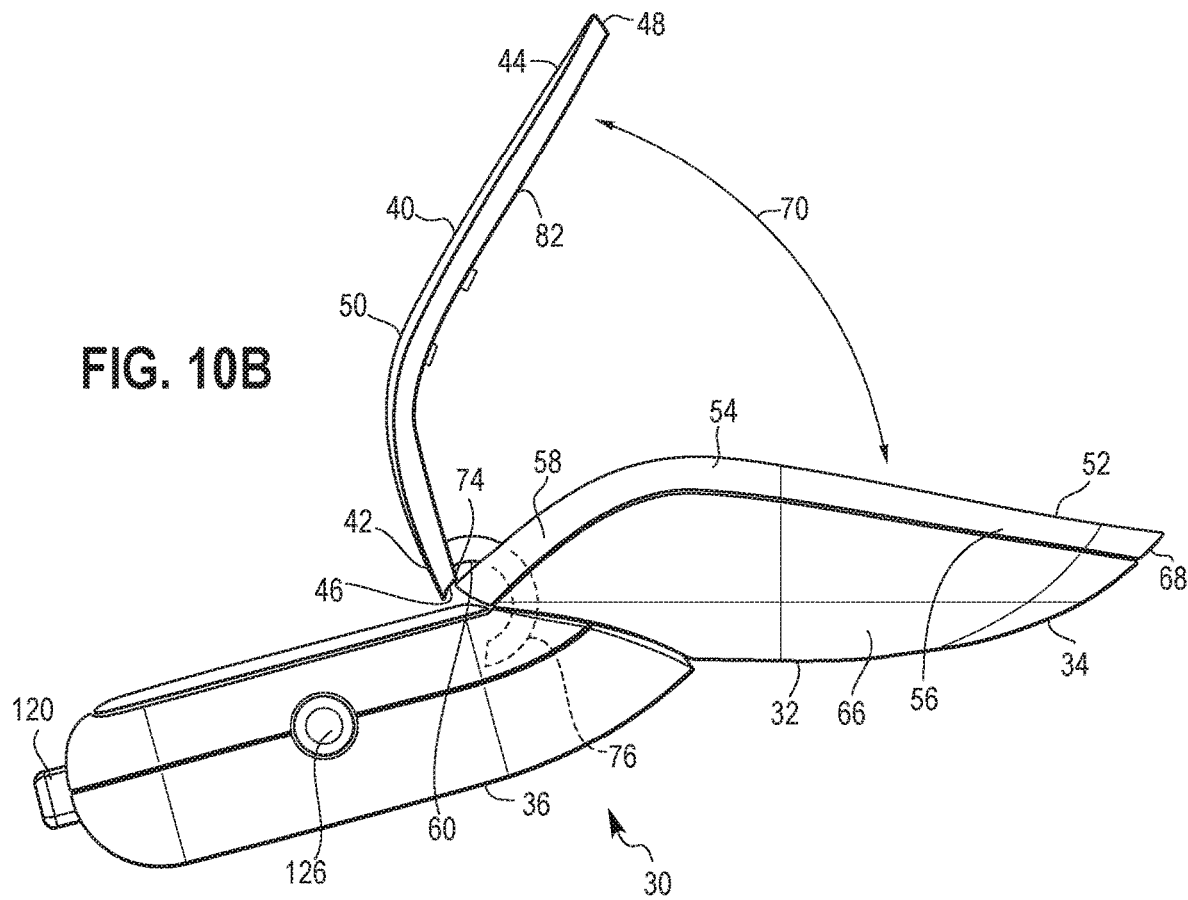

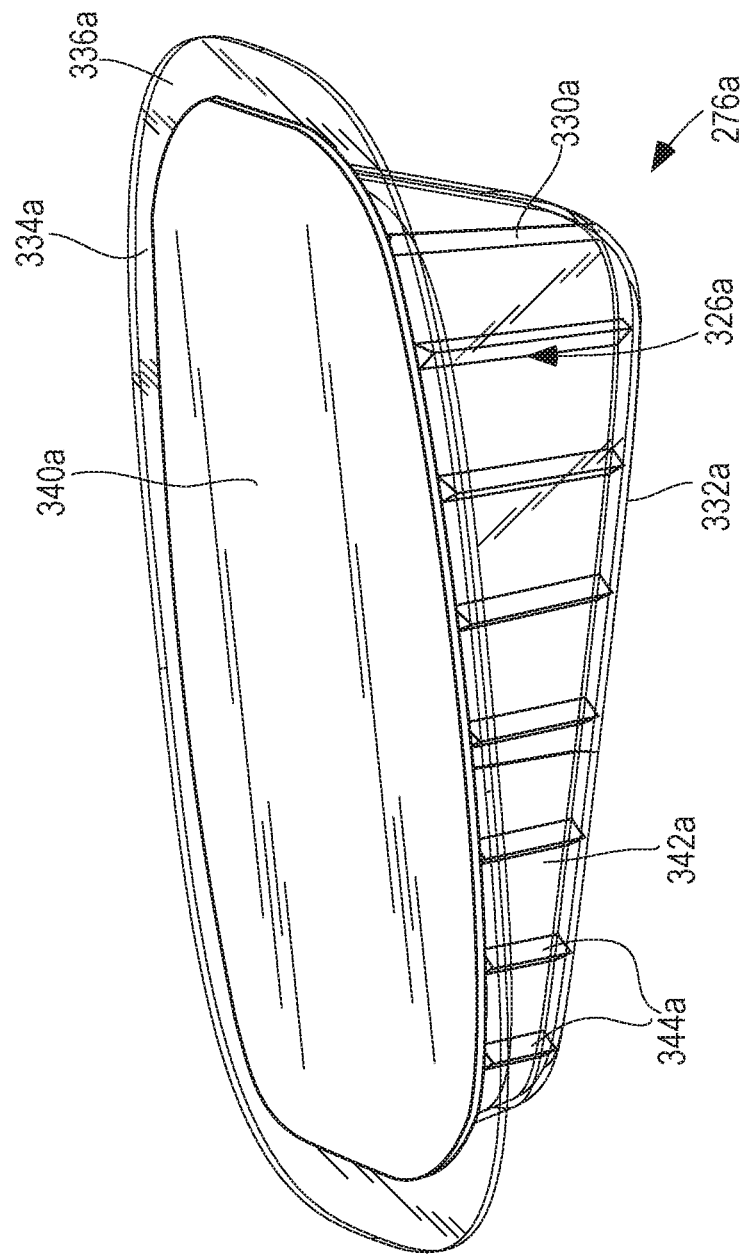

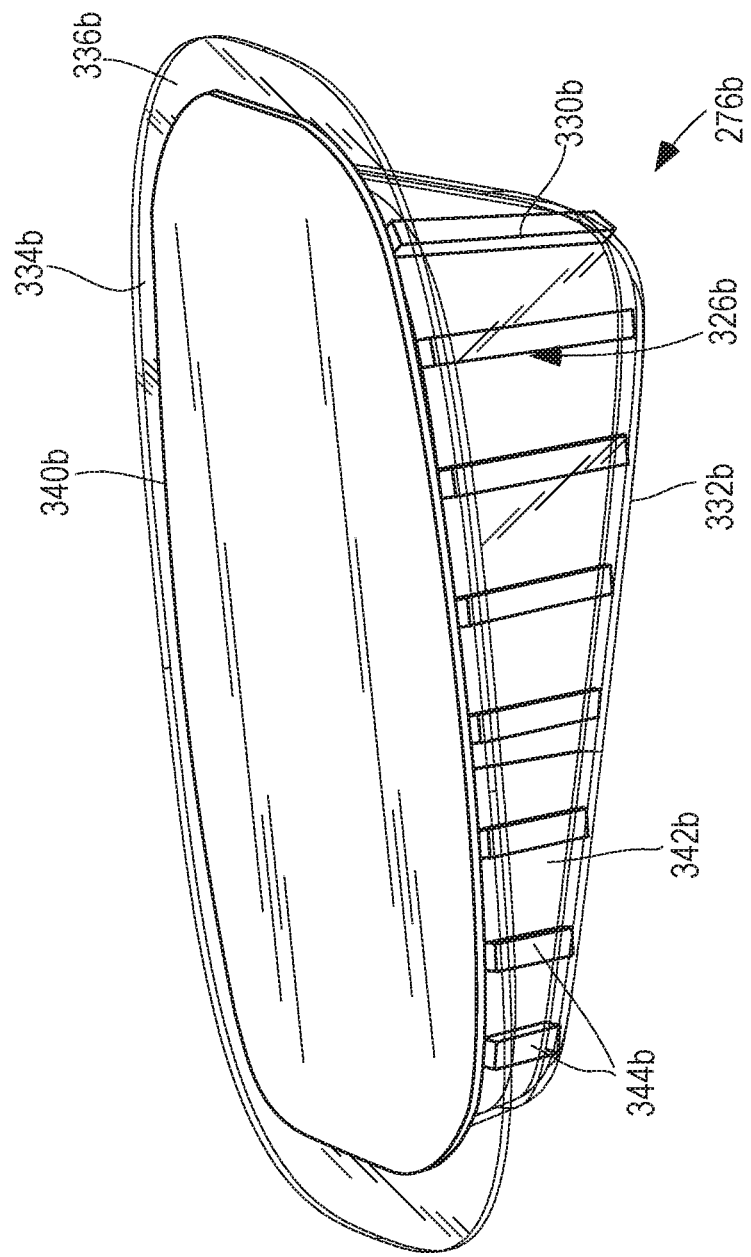

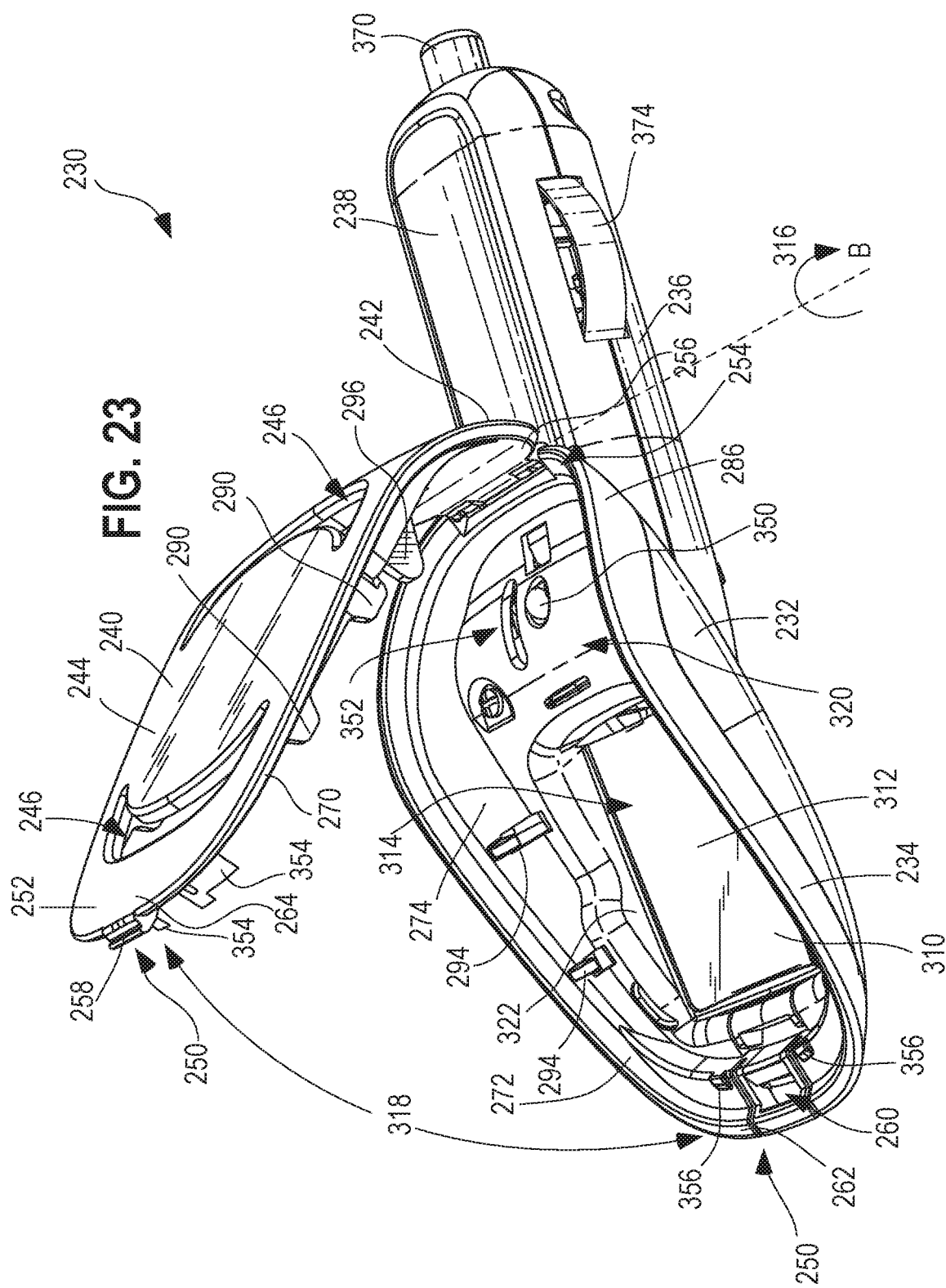

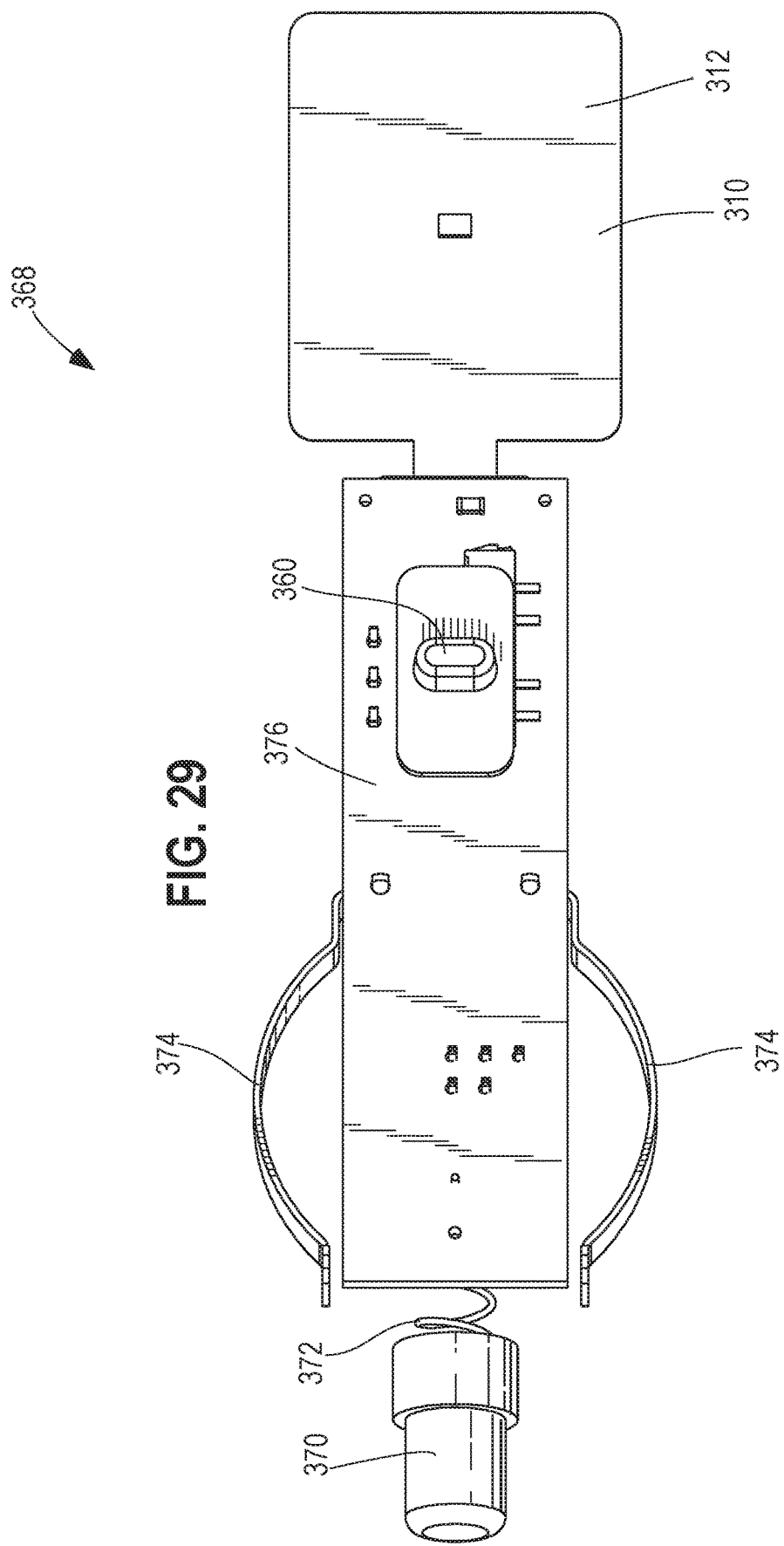

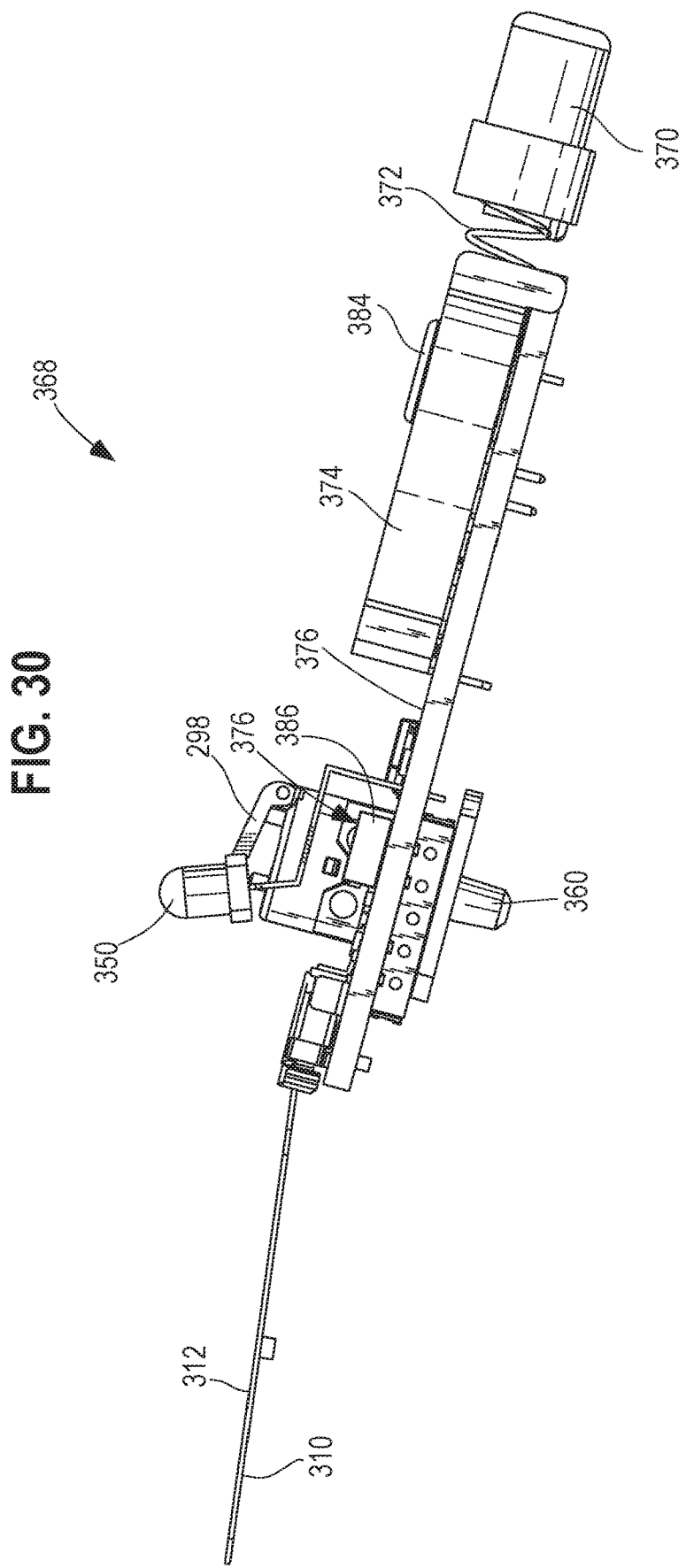

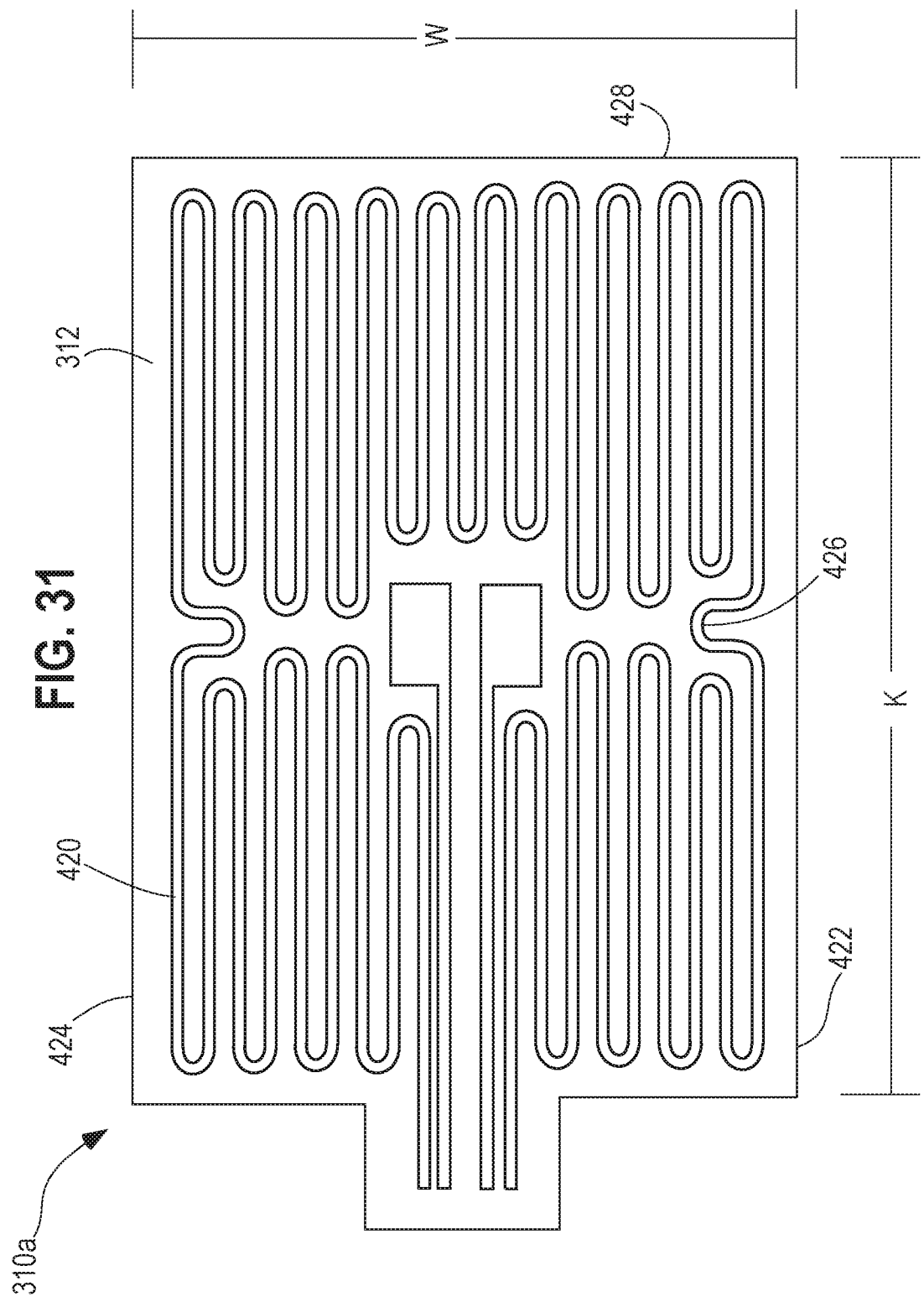

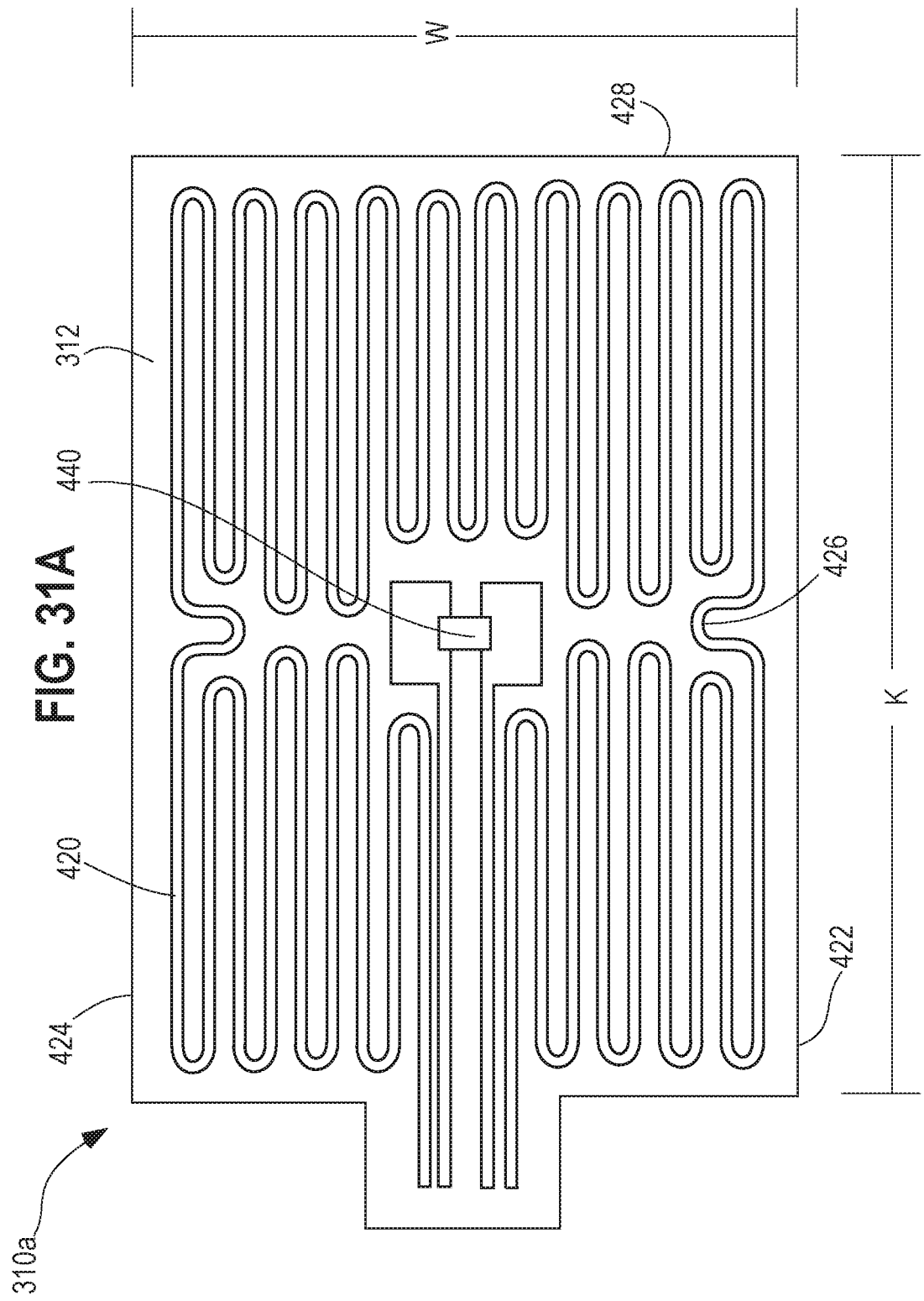

DISPENSER

CROSS REFERENCE TO RELATED APPLICATIONS

This application claims priority to U.S. Provisional Application No. 62/301,997, filed on Mar. 1, 2016.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present disclosure generally relates to a volatile material dispenser with a replaceable refill, and more specifically, to an air freshener and replaceable refill used in combination with a heat source.

2. Description of the Background of the Invention

Numerous types of dispensers exist for use in emitting various volatile materials. Of particular relevance to many individuals is the ability to emit a volatile material into a vehicle or personal transport. For example, many individuals utilize personal volatile emitting devices within their automobile, which may include air fresheners, odor eliminators, or any other volatile to assist in eliminating pests or to assist in cleaning.

Typical air fresheners used in automobiles are arranged to be used with a heat source, a refill or cartridge that receives heat from the heat source, and vents that expel a fragrancing volatile emanated from the cartridge to the surrounding atmosphere. Some air fresheners are arranged to plug into a 12V power socket provided within most automobiles.

However, some drawbacks exist with these types of air fresheners. Current air fresheners do not provide an adjustable fragrance. Further, typical devices and the cartridges used in them vary in their length of life and fragrance intensity according to the time of day and year and do not provide for controlled ambient emanation of the fragrance.

Therefore, a need exists for a heated air freshener that can control fragrance intensity and provide for controlled ambient emanation when an automobile is not in use.

SUMMARY OF THE INVENTION

In one aspect of the disclosure, a dispenser includes a housing including a cavity. A container is provided within the cavity and includes a volatile material therein. The dispenser further includes a resistive heating wire. The container is in thermal communication with at least a portion of the resistive heating wire.

In another aspect of the disclosure, a dispenser includes a housing having an electrical contact for communication with a power source in a vehicle, a lid movable between a closed state and at least one open state, a cavity within the housing, and a cartridge holding a volatile material within the cavity.

In yet another aspect of the disclosure, a dispenser includes a housing having a receptacle and a lid having two or more apertures, wherein the lid is coupled with the housing. A cartridge is provided within the receptacle. The cartridge has a reservoir holding a volatile material and a permeable membrane extends across the reservoir. A head space is defined between a bottom face of the lid and the permeable membrane.

BRIEF DESCRIPTION OF THE DRAWINGS

FIG. 9A is a top left isometric view of the dispenser of FIG. 1 in a closed position;

FIG. 9B is a top left isometric view of the dispenser of FIG. 9A in a first open position;

FIG. 10A is a side elevational view of the dispenser of FIG. 9B;

FIG. 10B is a side elevational view of the dispenser of FIG. 9A in a second open position;

FIG. 22A is a top right isometric view of yet another cartridge for use with the dispensers disclosed herein;

FIG. 22B is a top right isometric view of still another cartridge for use with the dispensers disclosed herein;

FIG. 23 is a top right isometric view of the dispenser of FIG. 17 with the lid in an open configuration and a cartridge removed for clarity;

FIG. 29 is a bottom plan view of the electrical assembly of FIG. 28;

FIG. 30 is a side elevational view of the electrical assembly of FIG. 28;

FIG. 31 is a schematic view of one embodiment of a heater element;

FIG. 31A is a schematic view of another embodiment of a heater element; and

Other aspects and advantages of the present invention will become apparent upon consideration of the following detailed description, wherein similar structures have similar reference numerals.

DETAILED DESCRIPTION

Figure 1:
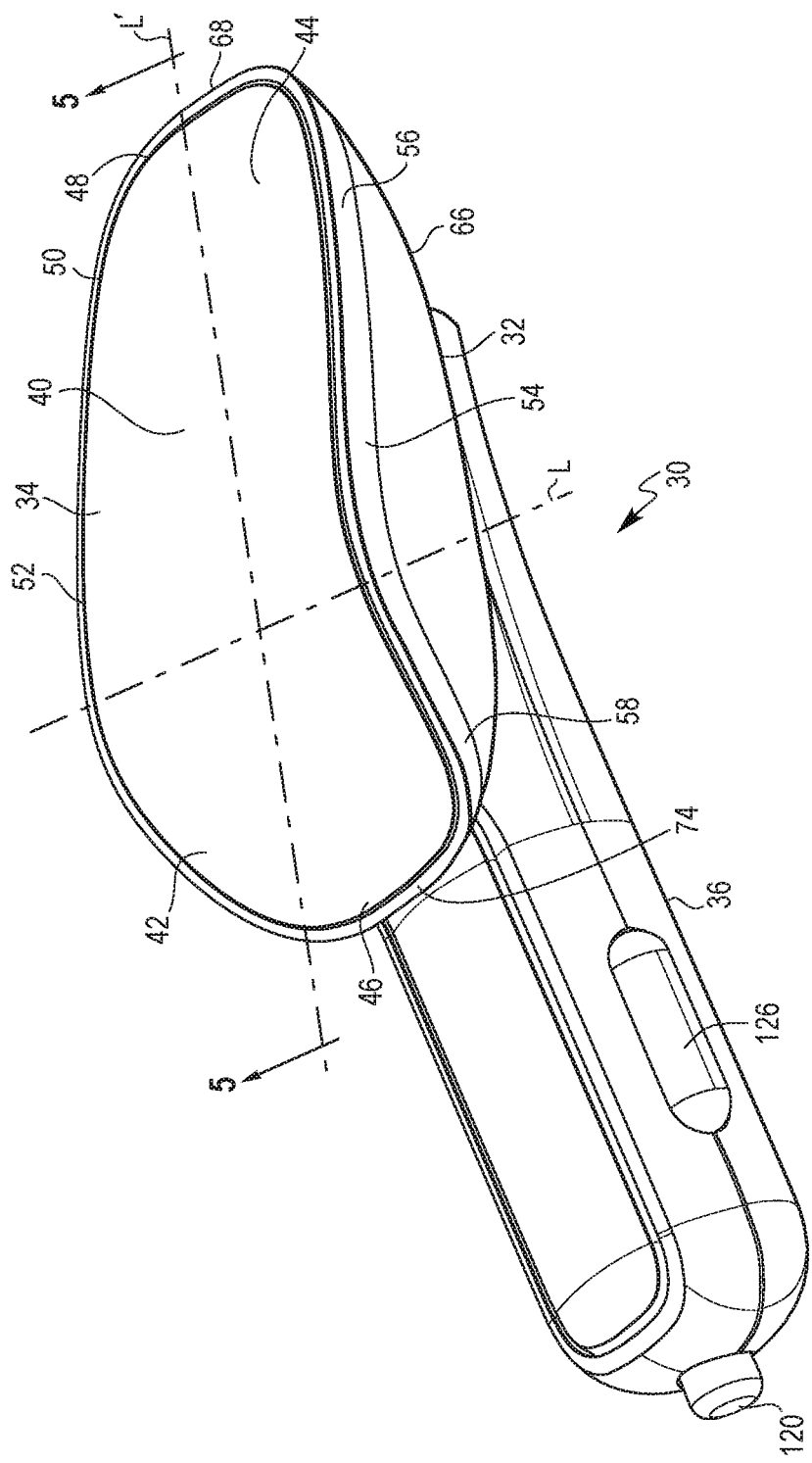
FIG. 1 is a top left isometric view of a dispenser according to one embodiment.
Figure 2:
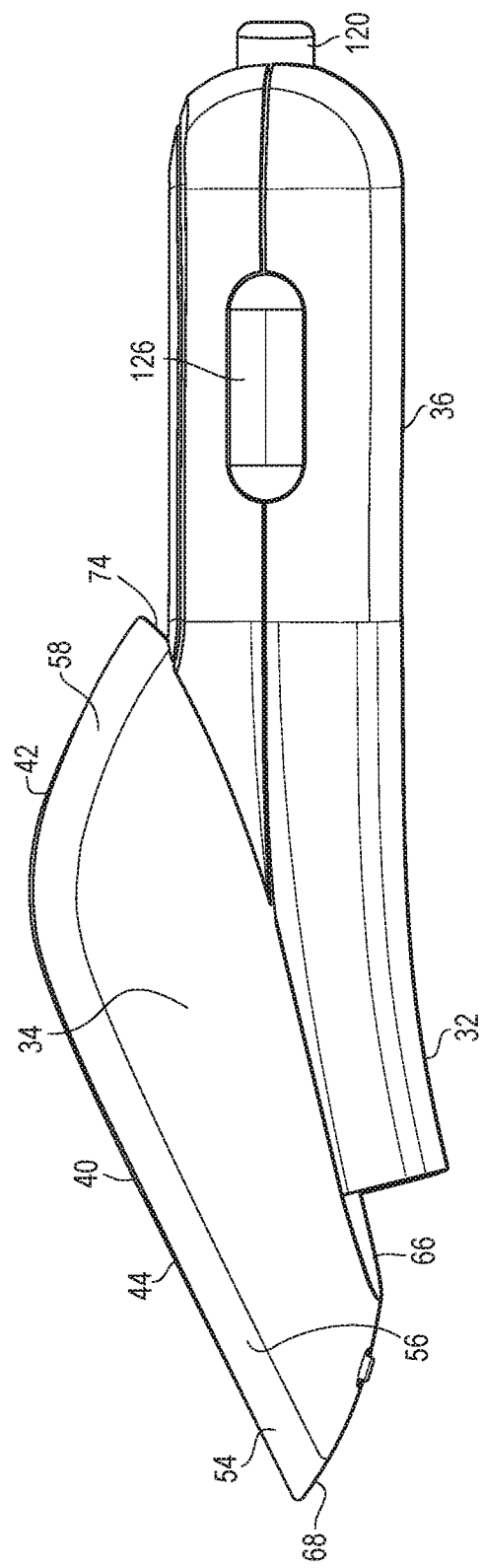
FIG. 2 is a side elevational view of the dispenser of FIG. 1.

With reference to FIGS. 1-3B, a dispenser 30 is shown. The dispenser 30 includes a housing 32 having a first portion 34, a second portion 36, and a lid 40. For purposes of the present description, the dispenser 30 is provided for dispensing an air freshening volatile into the interior of a vehicle, such as an automobile. However, any volatile material may be utilized for emission into the interior of a vehicle with the dispenser 30 and any alternative embodiments. Further, it is contemplated that the dispenser 30 may be used in other personal transport mechanisms or in stationary structures where volatiles are desired to be emitted.

Figure 3A:
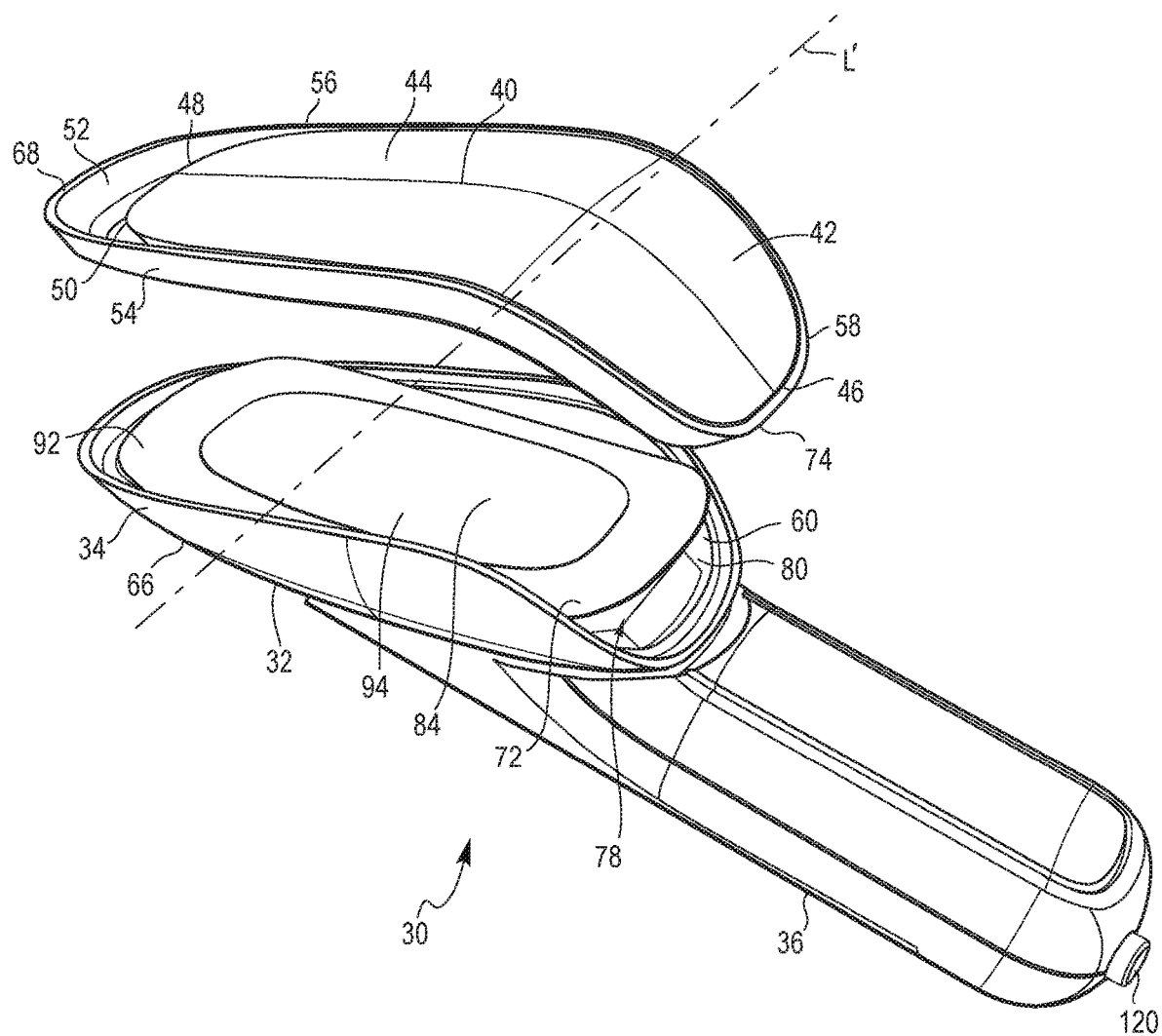
FIG. 3A is a partial, exploded, top right isometric view of a similar dispenser to the one shown in FIG. 1 with a lid and bezel shown separately and a hinging element removed.
Figure 3B:
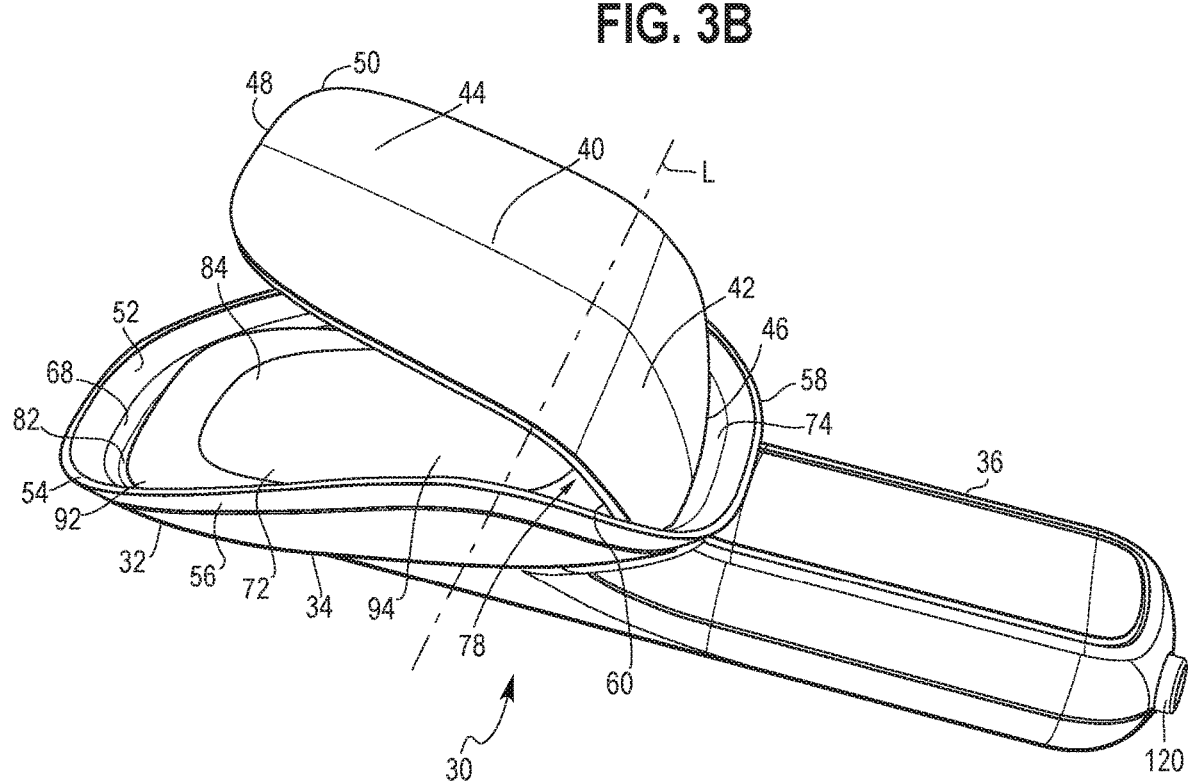
FIG. 3B is a top right isometric view of the dispenser of FIG. 3A.
Figure 6A:
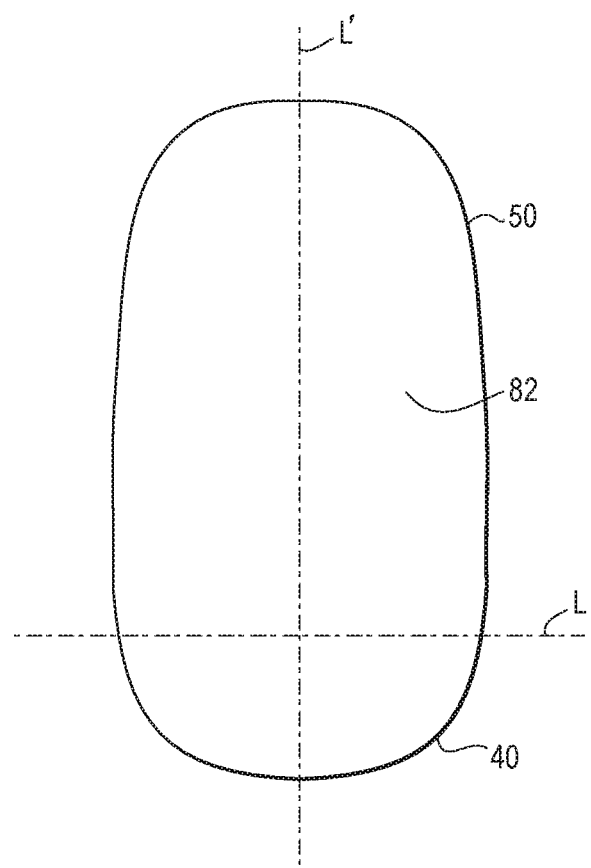
FIG. 6A is a top plan view of an inner surface of the lid of FIG. 5.

As shown in FIGS. 3A and 3B, the lid 40 includes a contoured surface with a rear portion 42 angled downwardly from a front portion 44 about a lid axis L (see FIGS. 1, 3A, and 3B). The axis L is disposed at about ⅓ of a length of the entire lid 40 measured about an axis L' (see FIG. 6) from a lowermost edge 46 thereof. In a preferred embodiment, the lowermost edge 46 of the rear portion 42 is angled from about 5 degrees to about 80 degrees, more preferably about 10 degrees to about 60 degrees, and most preferably about 15 degrees to about 50 degrees, from an uppermost edge 48 of the front portion 44, which is preferably part of a substantially flat surface of the front portion 44. With particular reference to FIG. 3A, a peripheral edge 50 of the lid 40 is shown flush with an inner wall 52 of a lid bezel 54, which is shown removed from the first portion 34 for purposes of clarity. FIG. 1 depicts a similar view of the dispenser 30, except that the lid 40 extends the entire extent of the bezel 54. It is contemplated, however, that in any of the embodiments a space may be provided between the peripheral edge 50 and the inner wall 52. FIGS. 1 and 3A further illustrate that the lid 40 and bezel 54 are generally contoured in a similar fashion, with a front portion 56 and a rear portion 58 of the bezel 54 angled in a similar manner as the lid 40. With reference to FIGS. 3A and 3B, the lid 40 is also provided with a hinge member 60.

Referring to FIGS. 9A-10B, the lid 40 is shown transitioning from a first closed state (FIG. 9A) to a second open state (FIGS. 9A-10B). It is envisioned that numerous open states may be utilized with the dispenser 30, including an infinite number of user-adjustable open positions that are afforded by manipulation of the lid 40 by the user about the hinge 60 to an open state of their choosing. However, in the present embodiment, the dispenser 30 is provided with a discrete number of open positions through conventional means known to those of ordinary skill to transition between pre-set closed, partially open, and fully open positions.

With reference to FIGS. 9B and 10A, a partially open or first position of the lid 40 is shown, which provides a first gap 64 between the lid 40 and a body 66 of the first portion 34 and the bezel 54 adjacent an end 68 thereof. With reference now to FIG. 10B, the lid 40 is shown in a fully open or second position to provide a second gap 70, which is larger than the first gap 64 and may allow easier access to a container, such as a cartridge 72, provided within the dispenser 30. It is further contemplated that more than three pre-set positions may be provided, for example, 4, 5, 6 or more, and/or that the lid 40 may be entirely removable from the housing 32.

In the embodiments illustrated in FIGS. 9A-10B, the hinge 60 is located in proximity to an opposite end 74 of the bezel 54 within the body 66 of the first portion 34. A path of rotation 76 is generally depicted for movement about axis R. The path of rotation 76 includes an arcuate length of about 10 cm to about 100 cm. It is envisioned that different lengths may be possible, however, it is preferred that the lid 40 be rotatably opened to a degree sufficient to allow for insertion of the cartridge 72. As previously noted, different types of hinges and other connecting means to connect lid 40 to the first portion 34 are also contemplated as are known to those skilled in the art.

Figure 5:
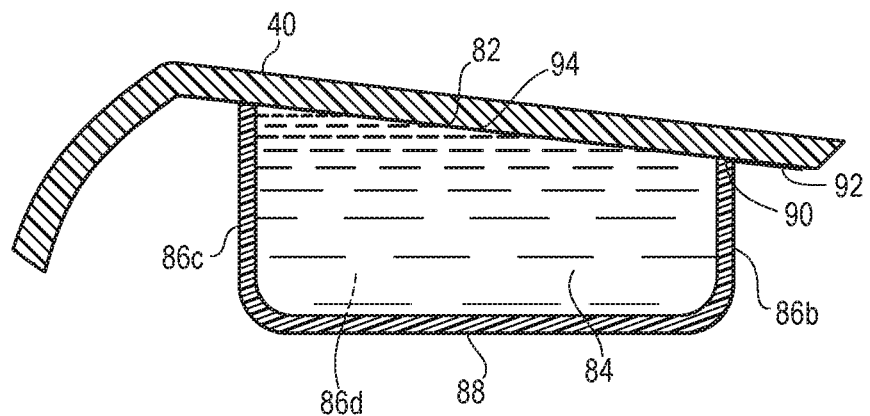
FIG. 5 is a partial, side sectional view of a lid and cartridge of the dispenser of FIG. 1 taken along the line 5-5 thereof, with portions removed for purposes of clarity.
Figure 6B:
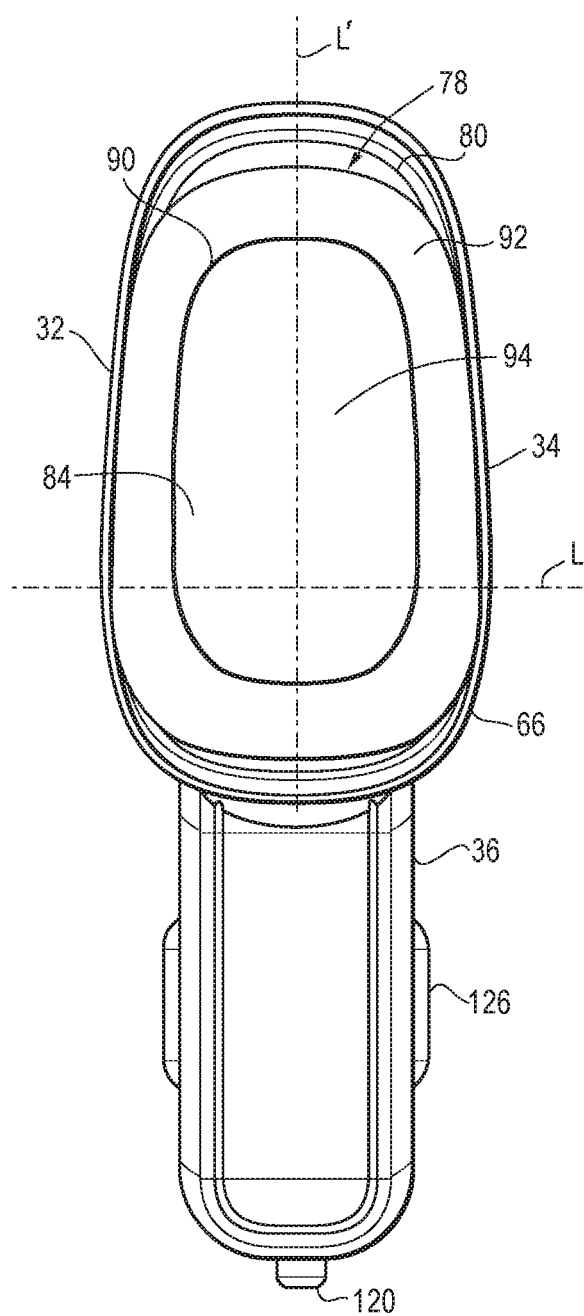
FIG. 6B is a top plan view of the dispenser of FIG. 1, with a lid removed and a cartridge provided within a cavity.

Referring to FIGS. 3A, 3B, and 6B, the body 66 of the front portion 34 is shown provided with a cavity 78. In the present embodiment, the cavity 78 is bounded by an inner wall 80 of the body 66, the inner wall 52 of the bezel 54, and an inner surface 82 (see FIGS. 5 and 6A) of the lid 40. When in an open state, e.g., see FIGS. 9B-10B, the gaps 64, 70 function as a vent for the dissipation of volatilized active ingredients, such as fragrance.

Figure 4:
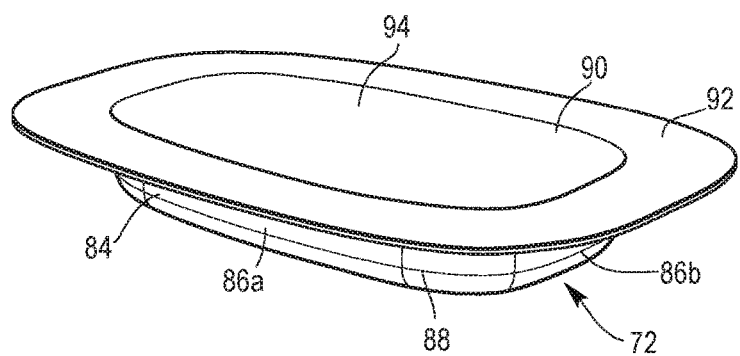
FIG. 4 is a top right isometric view of a cartridge for use with the dispensers disclosed herein.

Turning now to FIG. 4, one exemplary embodiment of the cartridge 72 for use with the dispenser 30 is shown. The cartridge 72 includes a reservoir 84 defined by a sidewall 86 and a bottom wall 88. In the present embodiment, the sidewall 86 may be generally characterized as having first, second, third, and fourth walls 86a, 86b, 86c, 86d, respectively, with curved edges. The sidewall 86 may be perpendicular to the bottom wall 88 or may be inclined relative thereto. In the present embodiment, an upper end 90 of the sidewall 86 terminates at a flange 92, which extends peripherally thereabout. The flange 92 preferably has a uniform thickness and may extend radially outward from the upper end 90 so that a width of the flange 92 is uniform thereabout. Regardless, it is contemplated that the flange 92 has a greatest radial width of about 0.5 cm to about 5 cm, and more preferably about 1 cm to about 3 cm. In the present embodiment, the upper end 90 of the sidewall is angled relative to the bottom wall 88, which may provide for greater volumetric capacity of the cartridge given the particular cavity 78 footprint and/or may allow for more effective or modified diffusion characteristics of the volatile based on the orientation of the dispenser 30 when used within a vehicle.

The cartridge 72 is sized to fit within the cavity 78, wherein the flange 92 is adapted to rest upon interior portions of the body 66. In a preferred embodiment, one or more support structures provide support to the flange 92, the sidewall 86, and/or the bottom wall 88 to provide for a secure retention of the cartridge 72 within the housing 32.

Still referring to FIG. 4, the cartridge 72 further includes a permeable membrane 94 that isolates the reservoir 84. More particularly, the permeable membrane 94 is attached to portions of the flange 92 to allow for diffusion of the volatile therethrough during an active state. It is also anticipated that a removable impermeable laminate (not shown) may be provided prior to activation of the cartridge 72, which extends over the permeable membrane to prevent diffusion of the volatile.

When the dispenser 30 is provided in a closed state, e.g., FIGS. 5 and 9A, the inner surface 82 of the lid 40 is juxtaposed with the permeable membrane 94. In a preferred embodiment, the inner surface 82 extends across the entirety of the permeable membrane 94 so that 100% of the surface area of the permeable membrane 94 covering the reservoir 84 is in physical contact with the inner surface 82. In a different embodiment, 60% to 90% of the surface area of the permeable membrane 94 covering the reservoir 84 is in physical contact with the inner surface 82. In another embodiment, the inner surface 82 is also juxtaposed with a portion or all of the flange 92 in the closed state. In a preferred embodiment, 100% of the surface area of the flange 92 is in physical contact with the inner surface 82. In a different embodiment, 20% to 70% of the surface area of the flange 92 is in physical contact with the inner surface 82. In some embodiments, the inner surface 82 comprises a polymer coating so that when it is in contact with the permeable membrane 94, an air-tight or vapor tight connection is able to form. In other embodiments, the inner surface 82 comprises a certain elasticity so that an air tight or vapor tight connection can be formed when pressing down against the permeable membrane 94. Effective closure of the dispenser 30 will allow for no, or substantially no, diffusion of the volatile through the permeable membrane 94. Such a seal will further prevent, or substantially prevent, volatile emission from the dispenser 30 when the dispenser is no longer powered or in an otherwise operational state, but may release volatile because of ambient heat or other conditions.

In an alternative embodiment, a second seal is also created between the peripheral edge 50 of the lid 40 and the inner wall 52 of the lid bezel 54. The second seal may be in addition to the first seal noted above between the lid 40 and the permeable membrane 94, or in lieu of it.

The reservoir 84 is filled with an active ingredient or volatile material comprising one or more components that is releasable to a local atmosphere through the permeable membrane 94. In certain embodiments, the active ingredient or volatile material is provided within a carrier material, which together are held within the reservoir 84 as a thickened liquid, gel, oil, resin, etc. In a preferred embodiment, the permeable membrane 94 is vapor permeable as opposed to liquid permeable and provides for the controlled release of all or a portion of the active ingredient or volatile material therethrough and into the ambient atmosphere (for example, in an automobile cabin). In certain embodiments, the active ingredient or volatile material can be a fragrance, insect repellent, or other product disposed within a carrier liquid, a deodorizing liquid, or the like. For example, the fluid may comprise OUST™, an air and carpet sanitizer for household, commercial, and institutional use, or GLADE®, a household deodorant, both sold by S. C. Johnson and Son, Inc., of Racine, Wis. The fluid may also comprise other actives, such as sanitizers, air and/or fabric fresheners, cleaners, odor eliminators, mold or mildew inhibitors, insecticides, and the like, or that have aroma therapeutic properties.

In one embodiment, the reservoir 84 is made of one or more polymer layers. The bottom stock can be resilient enough to fit into the body 66 and be retained therein. The polymer layers of the permeable membrane 94 are resilient enough to be sealed against the inside of the lid 40, as noted above, and heated by heaters without cracking, tearing, or suffering the effects of repeated heating. In some embodiments, the reservoir 84 may be a deformable reservoir or provide a life indicator that helps a user to know when the cartridge needs to be replaced. In other embodiments, the lid 40 is made of transparent materials so that a user can easily determine when to replace an empty reservoir. In yet other embodiments, the lid 40 contains a transparent window (not shown) to provide access for a user to view an empty reservoir and determine whether to refill the dispenser 30.

Figure 7:
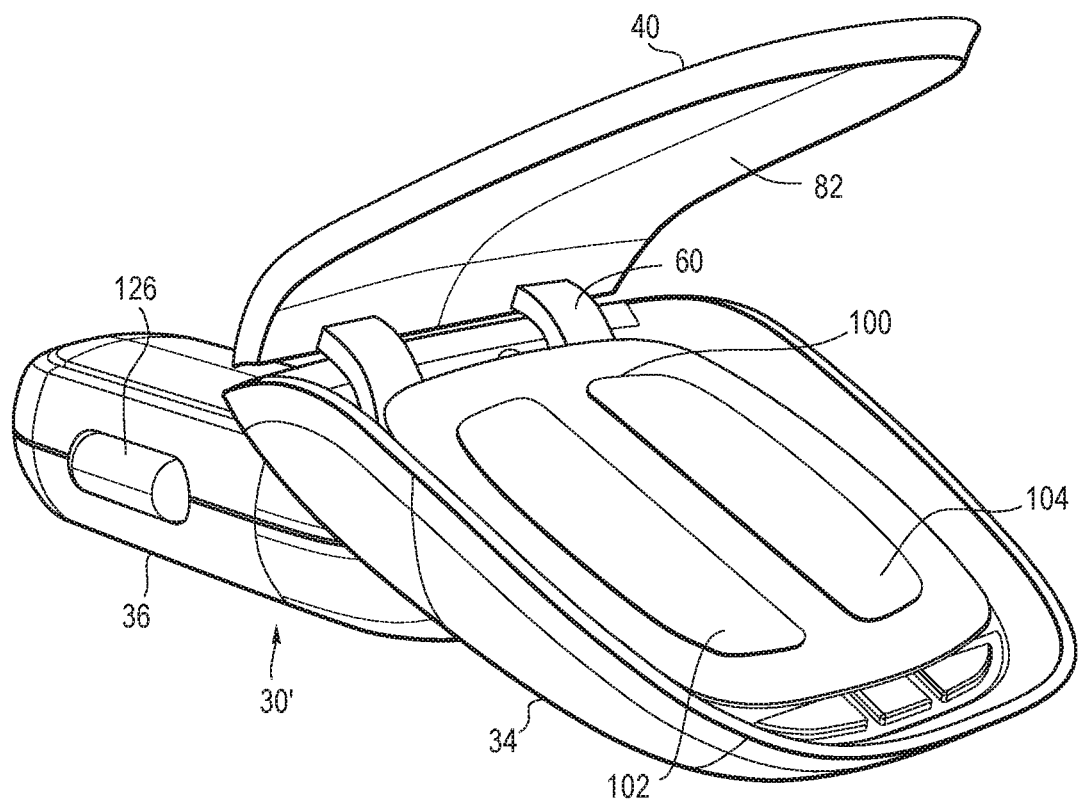
FIG. 7 is a top left isometric view of an alternative embodiment of a dispenser similar to the dispenser of FIG. 1, provided with a dual reservoir cartridge.
Figure 8:
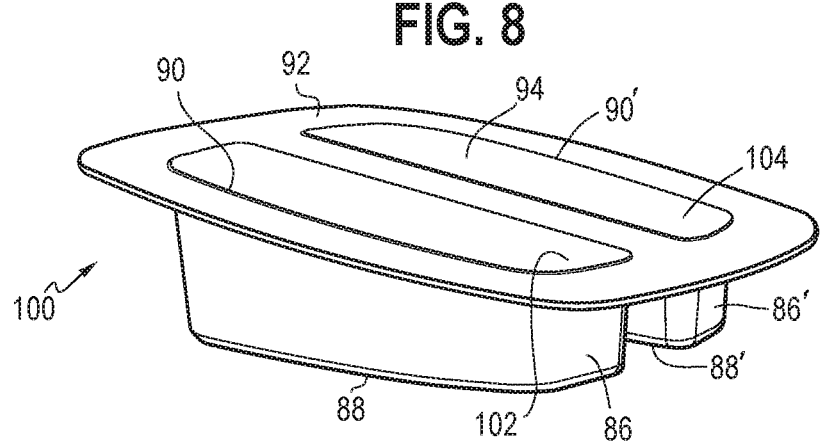
FIG. 8 is a top left isometric view of the cartridge of FIG. 7.
Figure 11:
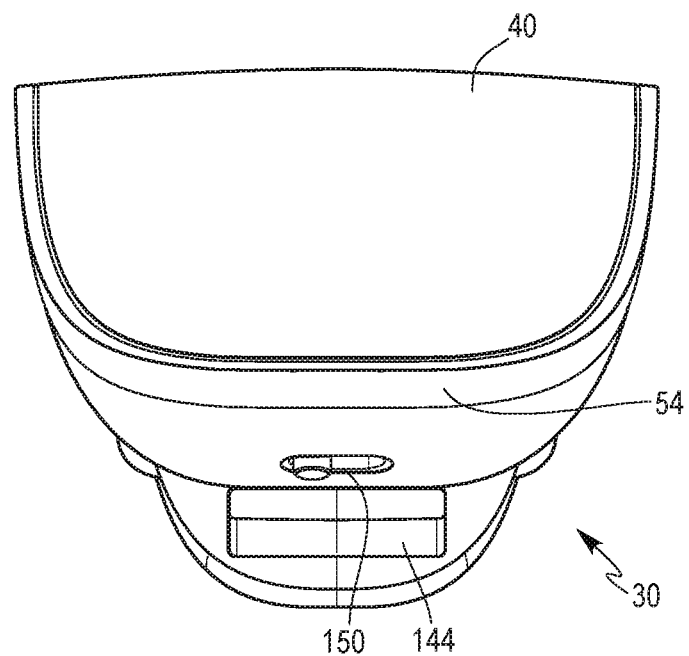
FIG. 11 is a front elevational view of the dispenser of FIG. 1 further showing a switch and a USB socket.
Figure 12:
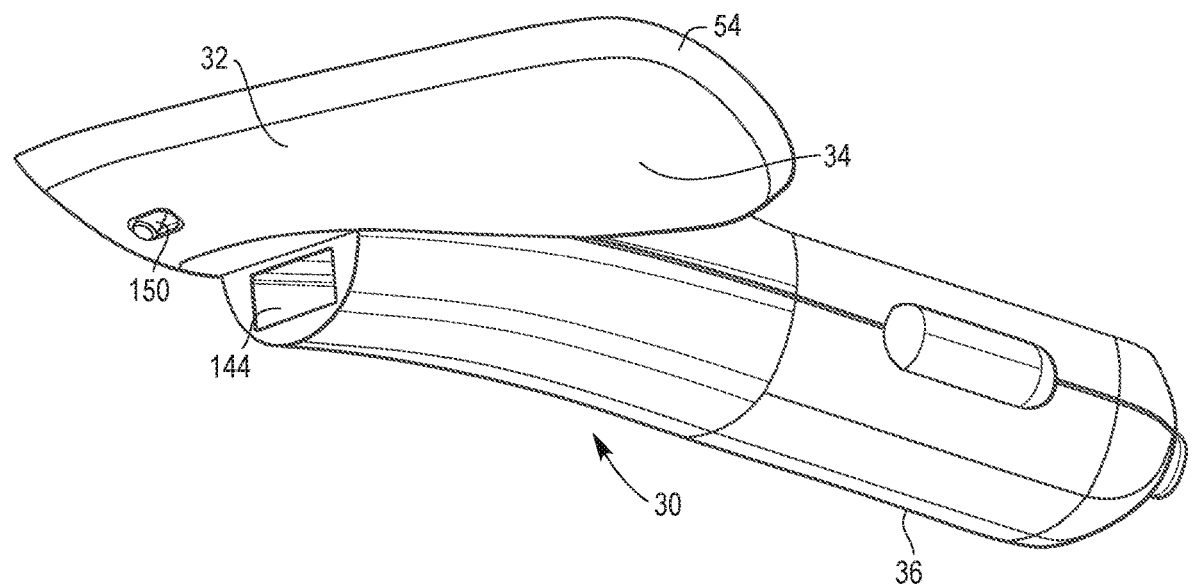
FIG. 12 is a front isometric view of the dispenser of FIG. 11.
Figure 13:
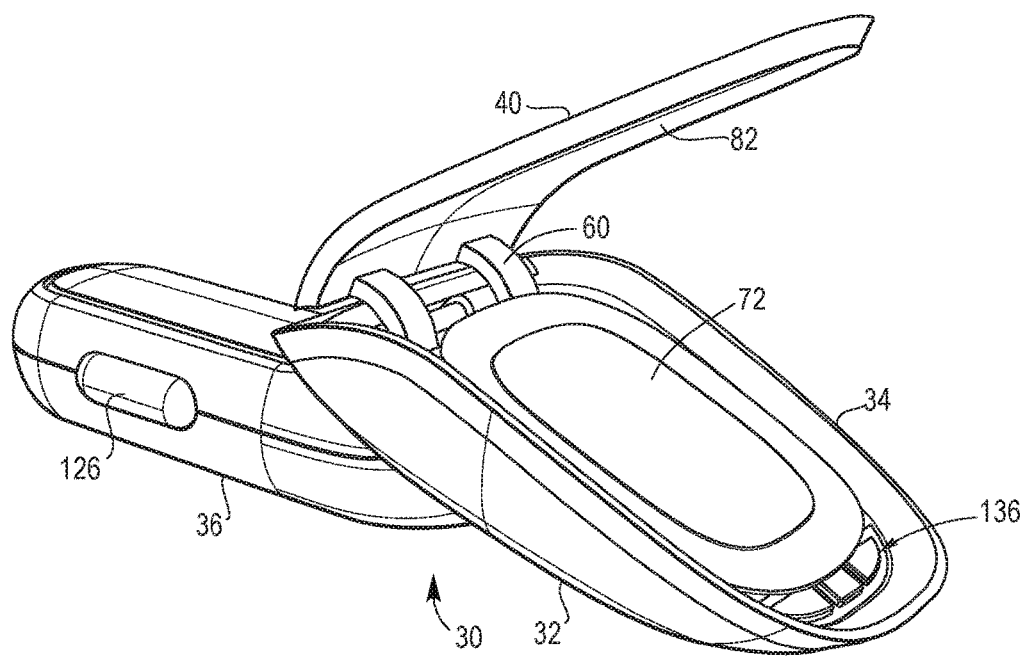
FIG. 13 is a top left isometric view of a dispenser similar to that shown in FIG. 1 with a lid open to show several LEDs and a hinging element.

Turning now to FIGS. 7 and 8, a dispenser 30' is depicted in conjunction with a cartridge 100. The cartridge 100 contains two reservoirs 102 and 104, wherein each reservoir includes a different type of volatile material so that two different functions may be performed at the same time or in some other sequence. For example, the reservoir 102 may contain a fragrance and the reservoir 104 may contain a sanitizer, odor eliminator, mold or mildew inhibitor, insect repellent or the like. In other embodiments, the two reservoirs 102, 104 may both contain different types of fragrance to permit multiple fragrancing in the surrounding environment. In another embodiment, the reservoirs 102, 104 contain the same volatile material to allow for a boost of the particular volatile and/or to act as a secondary supply of the volatile when the first volatile is used up. In a preferred embodiment, the reservoir 84 contains between about 2 cubic centimeters (CC) (or 2 grams (g)) and about 5 CC, or between about 3 CC and about 4 CC, or about 3.5 CC of the volatile material. Further, the reservoirs 102, 104 each contain between about 1.5 CC (or 1.5 g) and about 3 CC, or between about 1.75 CC and about 2.5 CC, or about 2.0 CC of the volatile material. It is also contemplated that the single or dual reservoir cartridges may contain more or less volatile material. Further, the number of reservoir compartments in a single cartridge disclosed herein are not limiting and may be broadened to three or more. Still further, instead of a single cartridge with two or more reservoirs, multiple discrete cartridges may be used.

Figure 14:
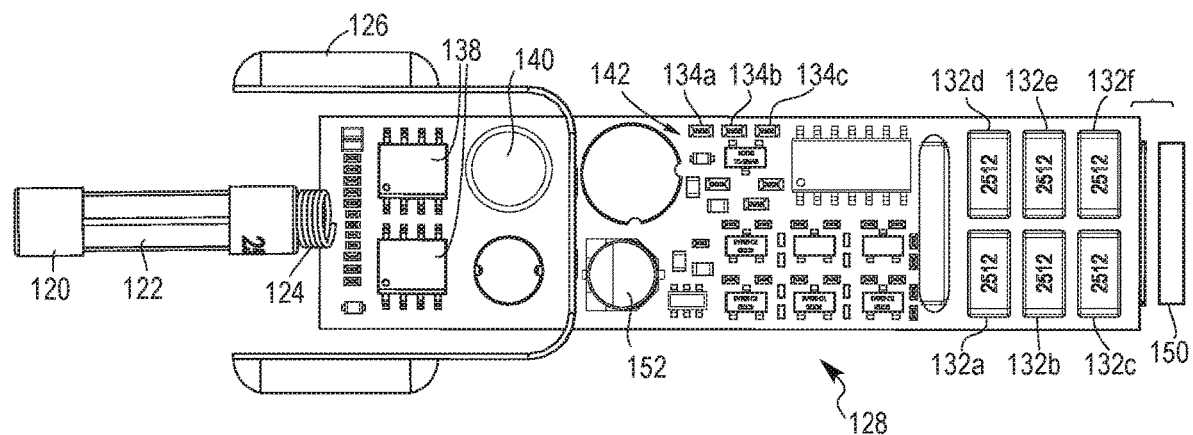
FIG. 14 is a top plan view of an electrical assembly for use with any of the dispensers herein.

Referring to FIGS. 11-15, components of the electrical assembly of the dispenser 30 will be described with greater particularity. With reference to FIG. 14, a positive contact 120 (see also FIG. 1) is shown for electrical communication with a contact within a vehicle (not shown), e.g., a lighter socket. FIG. 14 also depicts a fuse 122, a positive post 124, a common contact 126, and a printed circuit board (PCB)

128 in electrical communication with the positive post 124 and the common contact 126.

Figure 15:
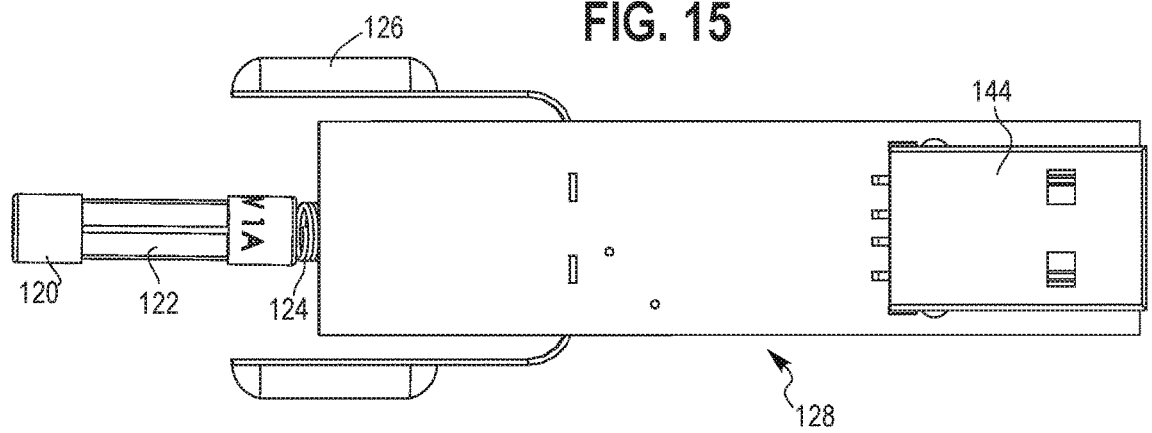
FIG. 15 is a bottom plan view of the electrical assembly of FIG. 14.

FIGS. 14 and 15 illustrate that the PCB 128 includes a heater 130, which may comprise one or more heating elements. In the present embodiment the heater 130 comprises a plurality of heater elements (132a-f), e.g., resistive heaters, arranged in two rows of three resistors each. The PCB 128 also includes a plurality of LED resistors (134a-c) corresponding to an LED indicator 136 (see FIG. 13). Further, the PCB 128 includes a microcontroller 138, a voltage booster 140, and an electric power sensor 142. In one particular embodiment, the PCB 128 is in electrical communication with a USB socket 144 (see FIGS. 11, 12, and 15).

In a preferred embodiment, the electrical assembly of the dispenser 30 is provided with a switch 150 for turning the dispenser 30 between on and off states, as well as at least two active operational settings. In other embodiments, the dispenser 30 is always in an on state and the switch 150 provides for the variation of two or more operational settings. In the present embodiment, the switch 150 is a slide switch movable between an off position, a first operational position, and a second operational position (see FIGS. 11 and 12). When the switch 150 is moved to the off position, electric power cannot flow from a power source to the PCB 128. As such, none of the LEDs transmit light (see FIG. 13). When the switch 150 is moved to one of the on positions, electric power flows from the power source and through the positive post 124 to the PCB 128, which results in the LED indicator 136 emitting a white light, a green light, or a light having any other color.

In an alternative embodiment, the switch 150 is provided with a greater number of operational states corresponding to varying increased steps in wattage, e.g., by increments of 1 W, or 0.5 W, or 0.2 W, or more or less. While a slide switch may be used, such an embodiment may be provided with a dial switch (not shown) for intuitive use by a user. The provision of greater operational states allows for the dispenser 30 to be imparted with a seemingly infinite variation in control of the dispenser 30, similar in manner to adjustment of a vehicles radio by a user. Therefore, the switch 150 contains a continuous output range of electric power and the switch 150 moves along the continuous range to adjust the flow of electric power in a linear manner. In some embodiments, the switch 150 is a touch switch regulated by touch sensors.

In certain embodiments, the flow of electric power from the positive post 124 to the plurality of heater elements 132a-f is controlled by a transistor 152. When the switch 150 is moved to an "on" position, the electric power is not necessarily transferred from the positive post 124 to the plurality of heater elements 132a-f. The electric power sensor 142 is used to detect a change of voltage from the power source when a user turns the automobile on or off. When a user turns the automobile on, a threshold value of voltage increase is reached, and the power sensor 142 sends a signal to the transistor 152 to conduct the electric power from the positive post 124 to the plurality of heater elements 132a-f. Thereafter, the plurality of heater elements 132a-f starts to generate heat. When a user turns a car off so that a threshold value of voltage decrease is reached, the power sensor 142 sends a signal to the transistor 152 to stop conducting the electric power from the positive post 124 to the plurality of heater elements 132a-f. Thereafter, the plurality of heater elements 132a-f stops generating heat. In certain embodiments, the electric power sensor 142 is controlled through smart phone Bluetooth™ technology. In other embodiments, the transistor 152 is a field-effect transistor (FET). Further, those skilled in the art will be able to use other types of transistors to open or close the electric channel between the positive post 124 and the plurality of heater elements 132a-f.

In yet other embodiments, the microcontroller 138 is used to record a user's driving habits, such as a schedule of going to work, dropping children off at school, going to lunch, etc. The microcontroller 138 is used to send a signal to the transistor 152 to either conduct electric power from the positive post 124 to the plurality of heater elements 132a-f or not, effectively starting the generation of heat to increase output of fragrance or stopping the generation of heat to decrease or stop the output of fragrance from the dispenser 30.

Figure 16:
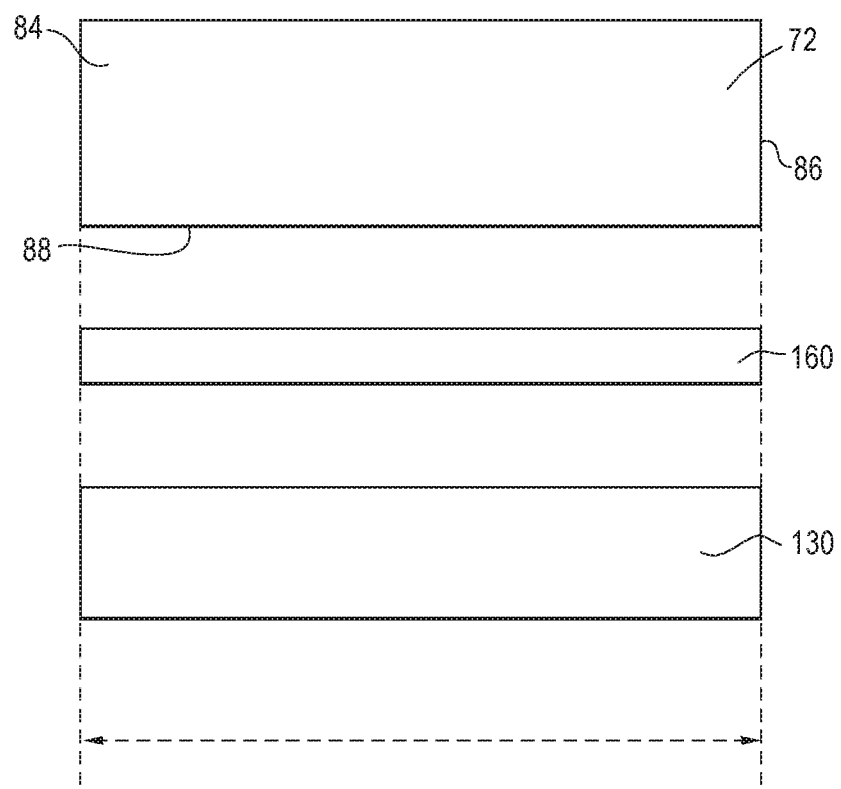
FIG. 16 is a schematic representation of the dispensers disclosed herein with an electrical assembly shown in relation to a cartridge and an optional deflector plate.

Referring to FIG. 16, the heater 130 comprising the plurality of heater elements 132a-f is disposed beneath the cartridge 72. More particularly, portions of the PCB 128 including the heater 130 are provided within the first portion 34 of the housing 32. Preferably, the heater 130 is provided entirely below the bottom wall 88 of the reservoir 84 of the cartridge 72. In one particular embodiment, a surface area of the bottom wall 88 is greater than a combined surface area of the heater 130 and defines a boundary within which the heater resides to provide for effective heat transfer, i.e., the heater 130 is below the cartridge 72 and does not extend beyond a perimeter of the bottom wall 88. In other embodiments, the heater 130 extends beyond a perimeter of the bottom wall 88 and/or includes heating elements adjacent the sidewall 86. Further, in certain embodiments, a heat deflector 160 is disposed between the heater 130 and the reservoir 84 to ensure optimal heating and emission of the volatile material. In all of the contemplated embodiments, the heater 130 is provided to assist in delivering various heating profiles to the reservoir 84 so that the volatile material contained therein may itself have various release profiles.

The number of heater elements can be changed and the disclosed number herein is not limiting. For example, the heater 130 may comprise one heater element, or 2-6 heater elements, or more than 6 heater elements, and may be provided in any manner within the housing 32, such as for example, in a single row of heater elements, or two rows of heater elements, or more than 2 rows of heater elements. Further, in lieu of a conventional resistance heater, one or more of the disclosed heater elements 132a-f may comprise a positive temperature coefficient (PTC) heater or any other heater element known to one of ordinary skill in the art. In other embodiments, the plurality of heater elements 132a-f comprises resistive components in which one or more have a different electric impedance.

In certain embodiments, the various heating profiles of the plurality of heater elements 132a-f are regulated by pulse-width modulation (PWM), which will be described for purposes of the present embodiment in connection with PTC heaters comprising the heater elements 132a-f. Movement of the switch 150 along the continuous electric power output range changes the voltage input from the power source. As a result, varying voltage input triggers different patterns of shutting off or turning on of certain heater elements 132a-f through PWM. Independent of user manipulation of the switch 150, PWM may be used as well. For example, when a car is initially turned on there may be a need to release a volatile material, such as a fragrance, quickly. Under the surge of voltage from the power source released upon startup of a vehicle, the dispenser 30 is programmed to turn on at least one PTC component to a specifically designated temperature and operate at that temperature by self-regulation. In certain embodiments, the voltage booster 140 is used in connection with at least one PTC component to achieve a certain temperature quickly. Therefore, the reservoir 84 and the permeable membrane 94 can release the volatile material in a substantially short amount of time, which ranges from about 5 seconds to 15 seconds. Moreover, in certain embodiments, the bottom 88 and/or the walls 86*a-d* of the reservoir 84 comprise thermally conductive materials, which reduce the amount of time needed to heat up or cool down the reservoir 84. In other embodiments, PWM may be used to program resistors with similar or different electric impedance to turn on or shut off at a certain time. Further, PWM can regulate the resistive heating of each resistor at a certain time. In certain embodiments, the PWM can be regulated via smart phone Bluetooth™ technology.

In certain embodiments, the PCB 128 further contains a sensor (not shown) for detecting changes in the ambient temperature, such as, for example, a thermistor. When the ambient temperature rises, the thermistor sends a signal to reduce heat generated by the heater elements, such as a PTC component, to maintain a constant release rate. On the other hand, when the ambient temperature decreases, the thermistor sends a signal to increase the heat generated by the heater elements, such as a PTC component, to maintain a constant release rate.

Further, release profiles may vary between different volatile materials based on the different types of active ingredients. In certain embodiments, the bottom wall 88 of the reservoir 84 includes at least one radio-frequency identification (RFID) tag, which can convey messages to the PCB 128 as to what kind of release profile is desired for maximizing the efficaciousness of the volatile material, e.g., a slow release rate or a fast release rate.

In certain embodiments, the dispenser 30 further includes a cartridge cooling unit (not shown) to control the temperature of the cartridge 72. Because high ambient temperatures may cause unwanted release of active ingredients, the cartridge cooling unit decreases the temperature of the reservoir 84 to reduce the volatizing rate of the volatile materials.

Further, in certain embodiments the dispenser 30 includes a volatized material dispersing unit (not shown) to ensure even distribution through the gaps 64 and 70. The dispersing unit may comprise a fan or any other suitable device known to those skilled in the art.

Moreover, in certain embodiments, the LED indicator 136 may serve to visually indicate by a certain color light or variation in light pattern that the cartridge 72 needs to be replaced or has been used up. For example, a yellow light may glow when the volatile material in the reservoir 84 has decreased to about half of the initial volume and a red light may glow when the cartridge 72 needs to be replaced.

Additionally, in certain embodiments the USB socket 144 (see FIGS. 11, 12, and 15) can be used to power other electronic devices within an automobile, such as, for example, charging mobile devices.

In other embodiments, herein provided volatile dispensers 30 may be configured to interact with one or more sensing devices, as well as other electronics or electrical components, such as resistors, LEDs, heaters, venting systems, and so forth. For example, the dispenser 30 may be provided with a switch or other detection mechanism that senses the physical presence of the cartridge 72 in the cavity 78 to allow for activation of the dispenser 30 and any of its electrical components. Conversely, if the cartridge is not detected, the dispenser 30 and any of its electrical components will not be activated. Further, other detection mechanisms may detect a fill state of the cartridge 72 and allow for the modification of the operation of the dispenser 30 and any of its electrical components.

Now referring to FIGS. 17-30, another embodiment of a dispenser 230 is shown. The dispenser 230 provides additional advantages in affording the release of some volatiles to the ambient environment during a non-use or non-operational state of the dispenser. However, it is contemplated that the dispenser 230 may be modified to include any of the structure or operational methodologies disclosed in connection with FIGS. 1-16. It is further contemplated that any variations disclosed in connection with the embodiments of FIGS. 1-16 may be used in connection with the dispenser 230.

The dispenser 230 includes a housing 232 having a first or top portion 234, a second or bottom portion 236, and a third or plug portion 238. The dispenser 230 also includes a lid 240. As discussed above, the described dispenser 230 is provided for dispensing an air freshening volatile into the interior of a vehicle, such as an automobile, but may similarly be used to dispense other materials or in other locations.

Figure 17:
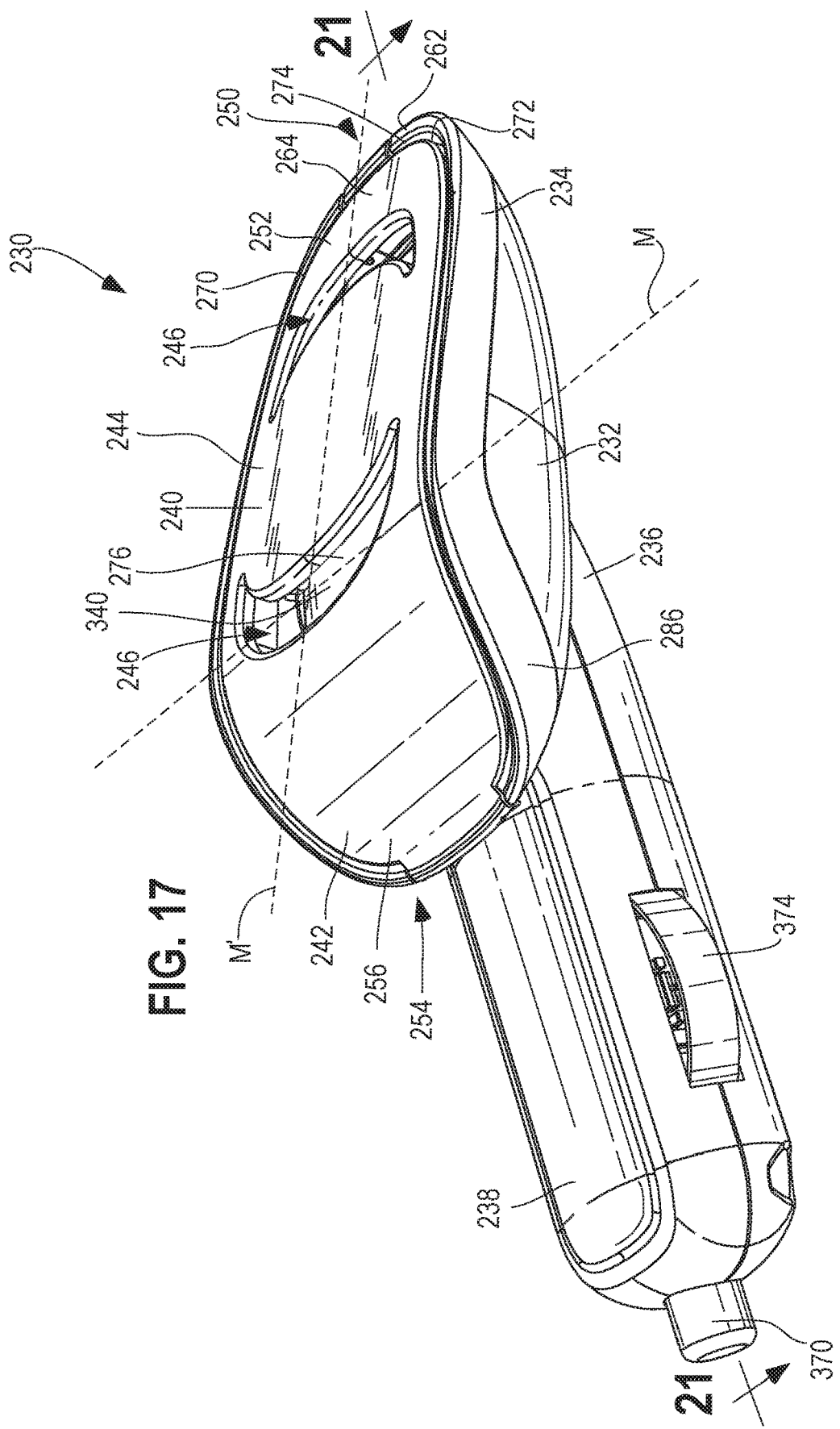
FIG. 17 is a top left isometric view of a dispenser having a lid according to another embodiment.
Figure 18:
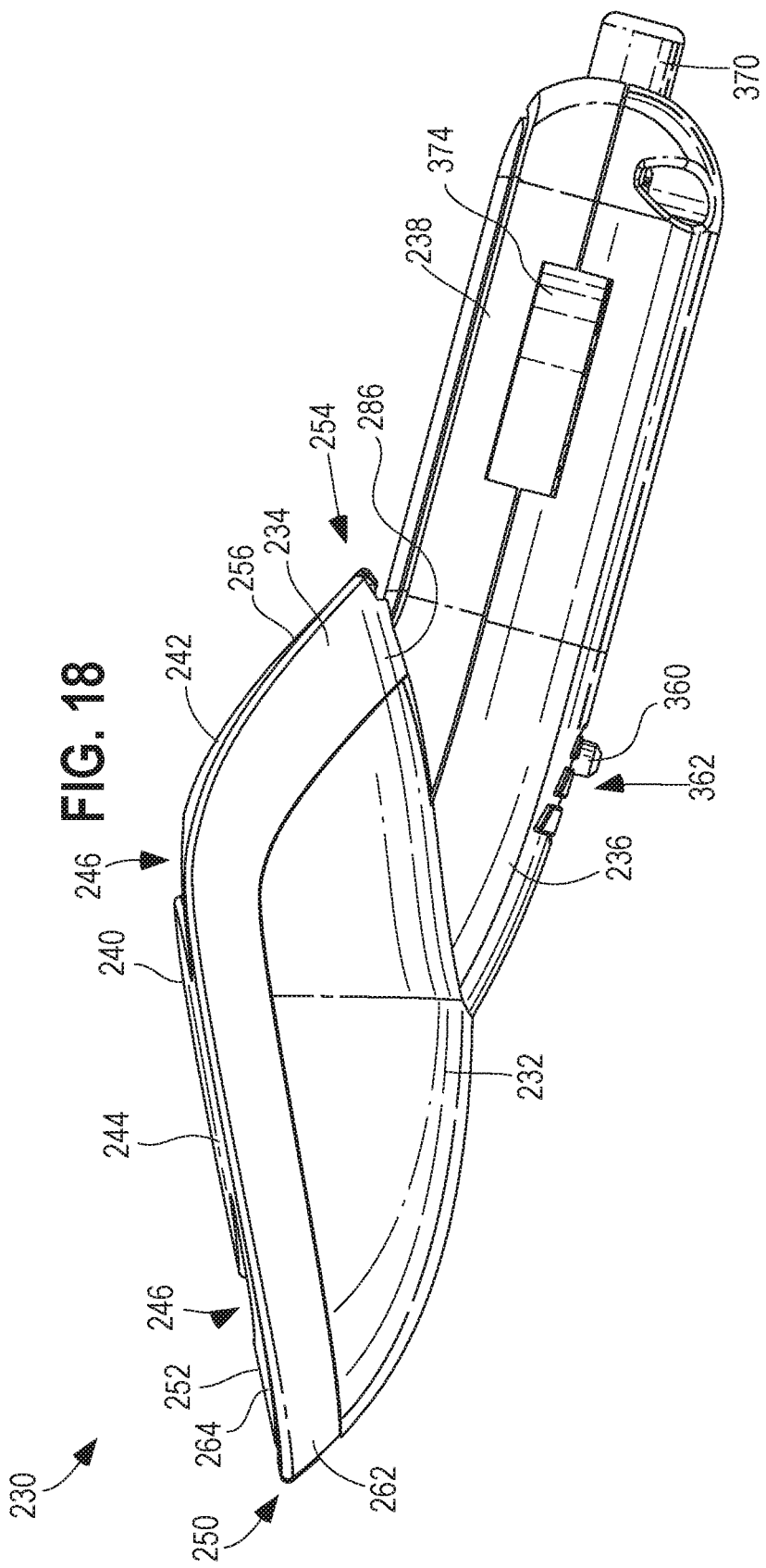
FIG. 18 is a side elevational view of the dispenser of FIG. 17.
Figure 19:
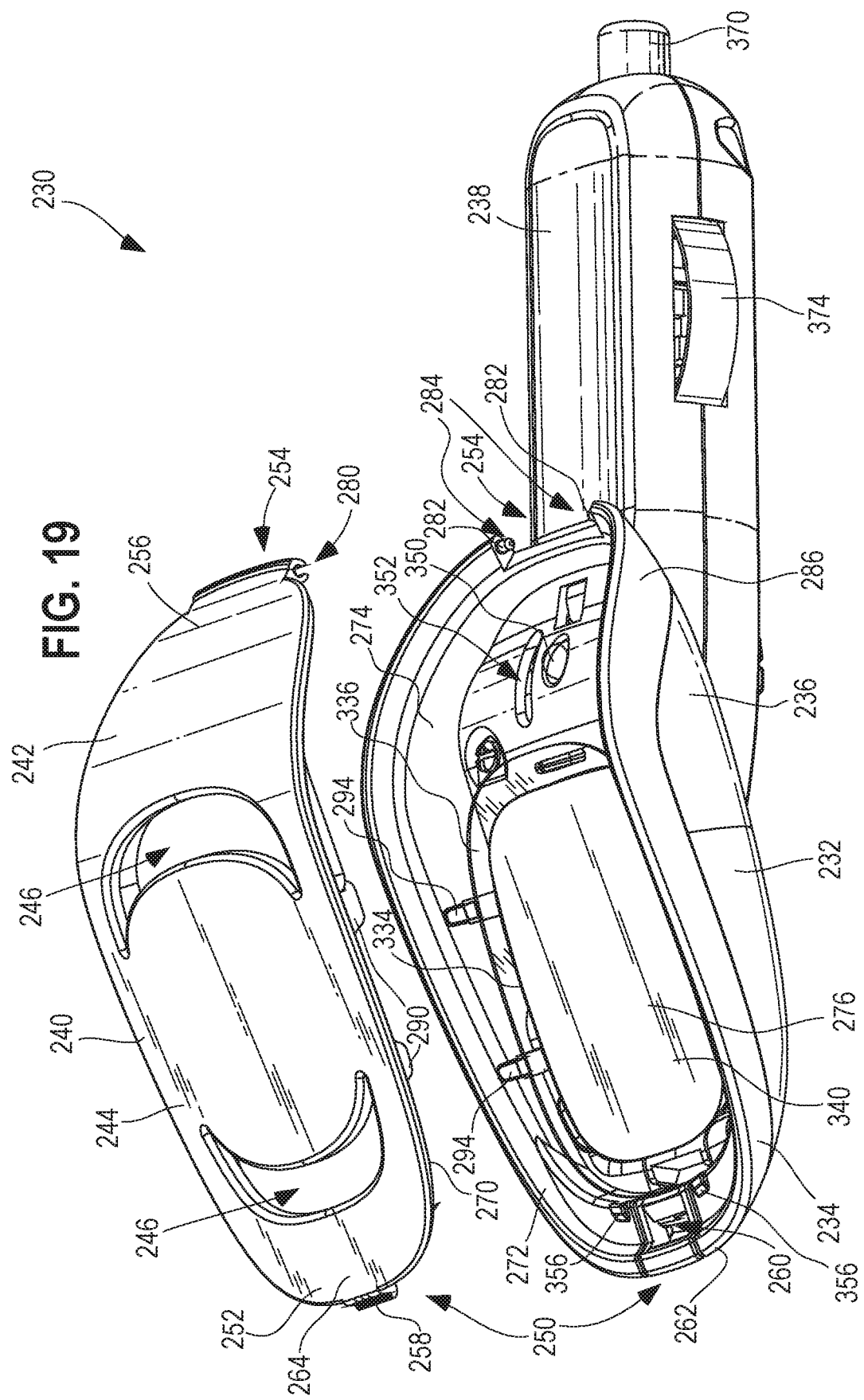
FIG. 19 is a partial, exploded, top right isometric view of a similar dispenser to the one shown in FIG. 17 with a lid shown separately.

As shown in FIGS. 17-19, the lid 240 includes a contoured surface with a rear portion 242 angled downwardly from a front portion 244, in a similar fashion as described above with respect to the dispenser 30. An axis M is disposed at about ⅓ of a length of the entire lid 240 measured about an axis M' (see FIG. 17) in a similar fashion as discussed with respect to axes L and L' above. The axis M' is a central axis that extends centrally through the lid 240. A central plane extends vertically through the axis M', and further extends vertically through the dispenser 230. A plurality of apertures 246 are provided in the lid 240 to facilitate airflow through portions of the dispenser 230. In the illustrated embodiment, the apertures 246 define a squared crescent shape, but the apertures may have alternative shapes. For example, the apertures 246 may be in the shape of a semi-circle, a semi-oval, a circle, an oval, a square, a triangle, a polygon, or any other shape known to those of ordinary skill in the art. Further, the apertures 246 may have the same size and/or shape, or may have different sizes and/or shapes. Still further, in some embodiments, only a single aperture 246 may be included. In other embodiments, three or more apertures are provided. The apertures 246 allow the surrounding atmosphere to be in fluid communication with interior portions of the housing 232.

Still referring to FIGS. 17-19, a push to open latch or retention mechanism 250 is provided adjacent a front end 252 of the front portion 244 of the lid 240, while a hinge 254 is provided adjacent a rear end 256 of the rear portion 242. In the illustrated embodiment, the retention mechanism 250 includes a catch 258 (see FIG. 19) that is formed with the lid 240, and an opening 260 (see FIG. 19) within a front end 262 of the housing 232 that receives the catch 258. The catch 258 is provided adjacent a depressible area or actuation portion 264, which is depressible by a user in order to release the lid 240 from engagement with the housing 232. In some embodiments, the retention mechanism 250 may include a clasp, a hasp, a fastener, or another latch mechanism that is capable of holding the lid 240 in place during use of the dispenser 230, and that allows a user to disengage the lid 240 by pressing or otherwise manipulating the actuation portion 264 adjacent the front end 252 of the lid 240.

Figure 20:
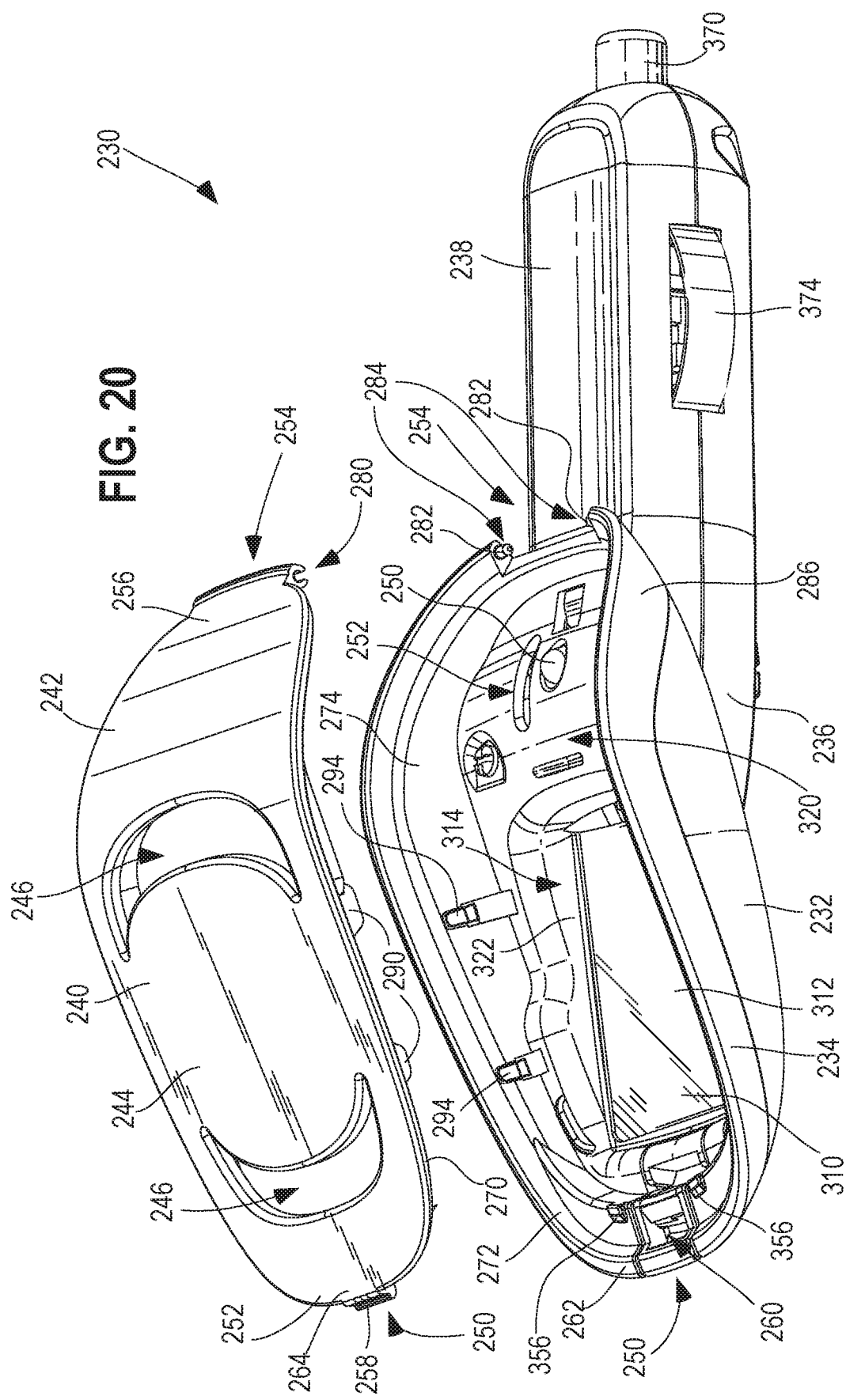
FIG. 20 is a partial, exploded, top right isometric view of a similar dispenser to the one shown in FIG. 17 with a lid shown separately and with a cartridge removed.

With particular reference to FIG. 17, a peripheral edge 270 of the lid 240 is shown flush with a ledge 272 (or bezel) of an inner wall 274 of the top portion 234. With reference to FIG. 19, the lid 240 is shown removed from the top portion 234, and in FIG. 20 a similar view is depicted except that a container, such as a cartridge 276, is also removed. FIGS. 19 and 20 further illustrate that the lid 240 and the top portion 234 are generally contoured in a similar fashion, with the top portion 234 angled in a similar manner as the lid 240.

With reference still to FIGS. 19 and 20, the hinge 254 is depicted as comprising one or more bores 280 and protrusions 282. In the illustrated embodiment, two protrusions 282, which collectively form a hinge pin 284, extend from a rear end 286 of the top portion 234. The bore 280 is provided within the rear end 256 of the rear portion 242 of the lid 240 and engages with the protrusions 282. The protrusions 282 form a snap fit engagement with the bore 280 to form the hinge 254. In the illustrated embodiment, the bore 280 may be characterized as a partial bore, as the continuity of the cylindrical section is interrupted to allow for the snap-fitment of the protrusions 282 into the bore 280. In alternative embodiments, the hinge pin 284 formed by the protrusions 282 may be one continuous pin rather than two protrusions and/or the bore 280 may comprise two or more discrete sections for engagement with the hinge pin 284. It is further contemplated that other types of hinges may also be used.

Figure 21:
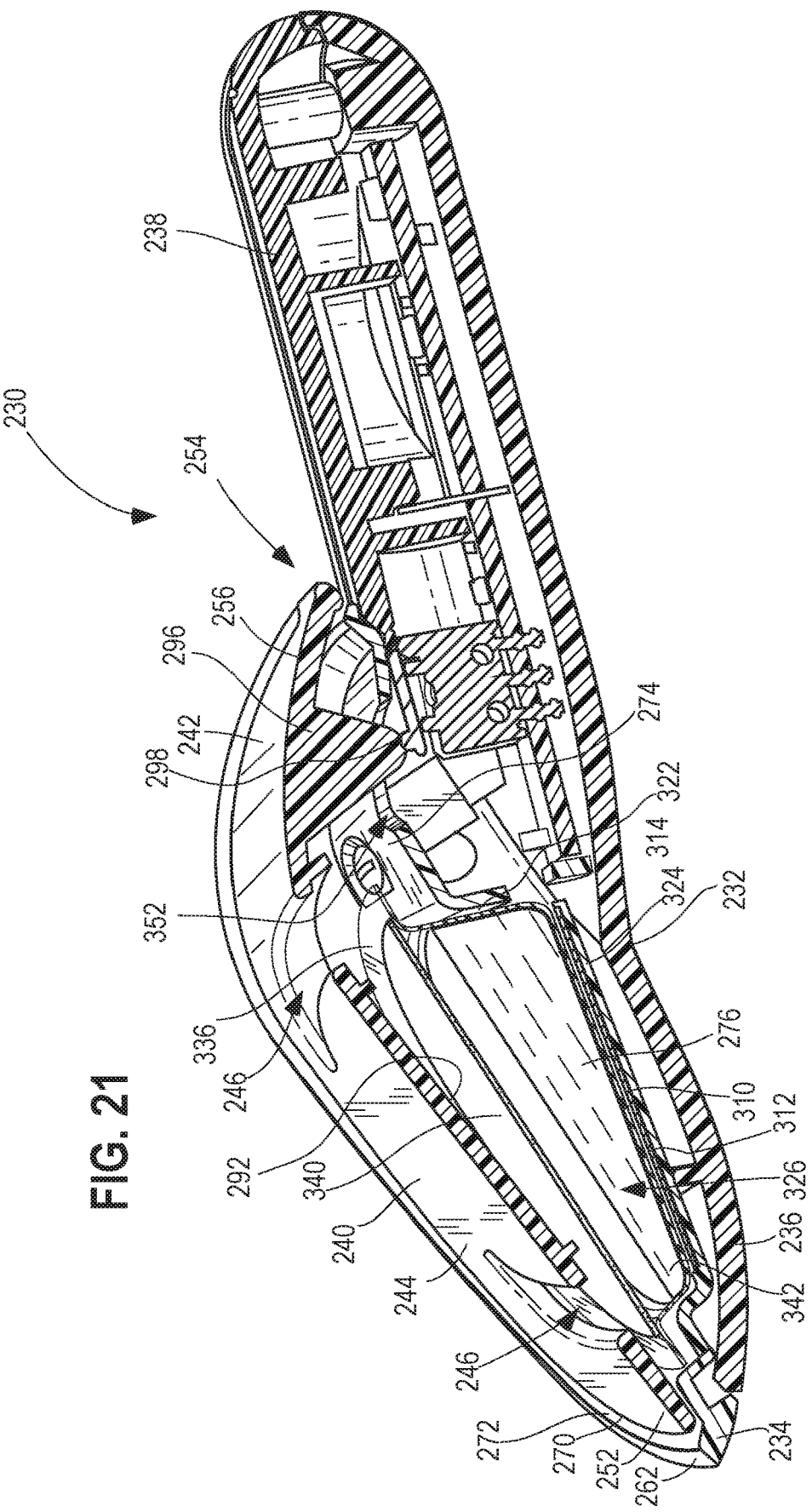
FIG. 21 is an isometric cross sectional view of the dispenser of FIG. 17 taken through line 21-21 of FIG. 17.
Figure 24:
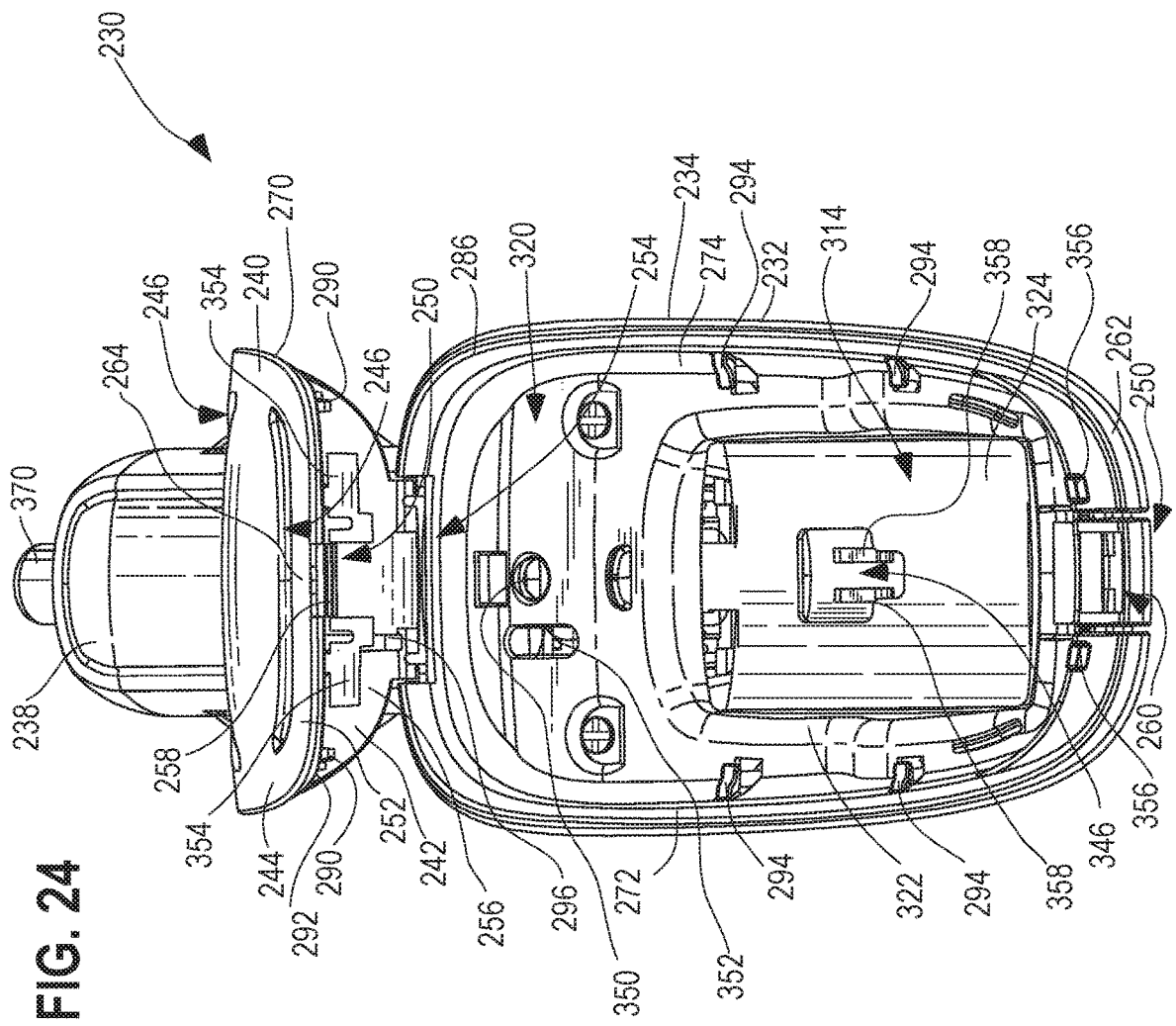
FIG. 24 is a top plan view of the dispenser of FIG. 17 with the lid in an open configuration with a cartridge and a heater element removed for clarity.
Figure 25:
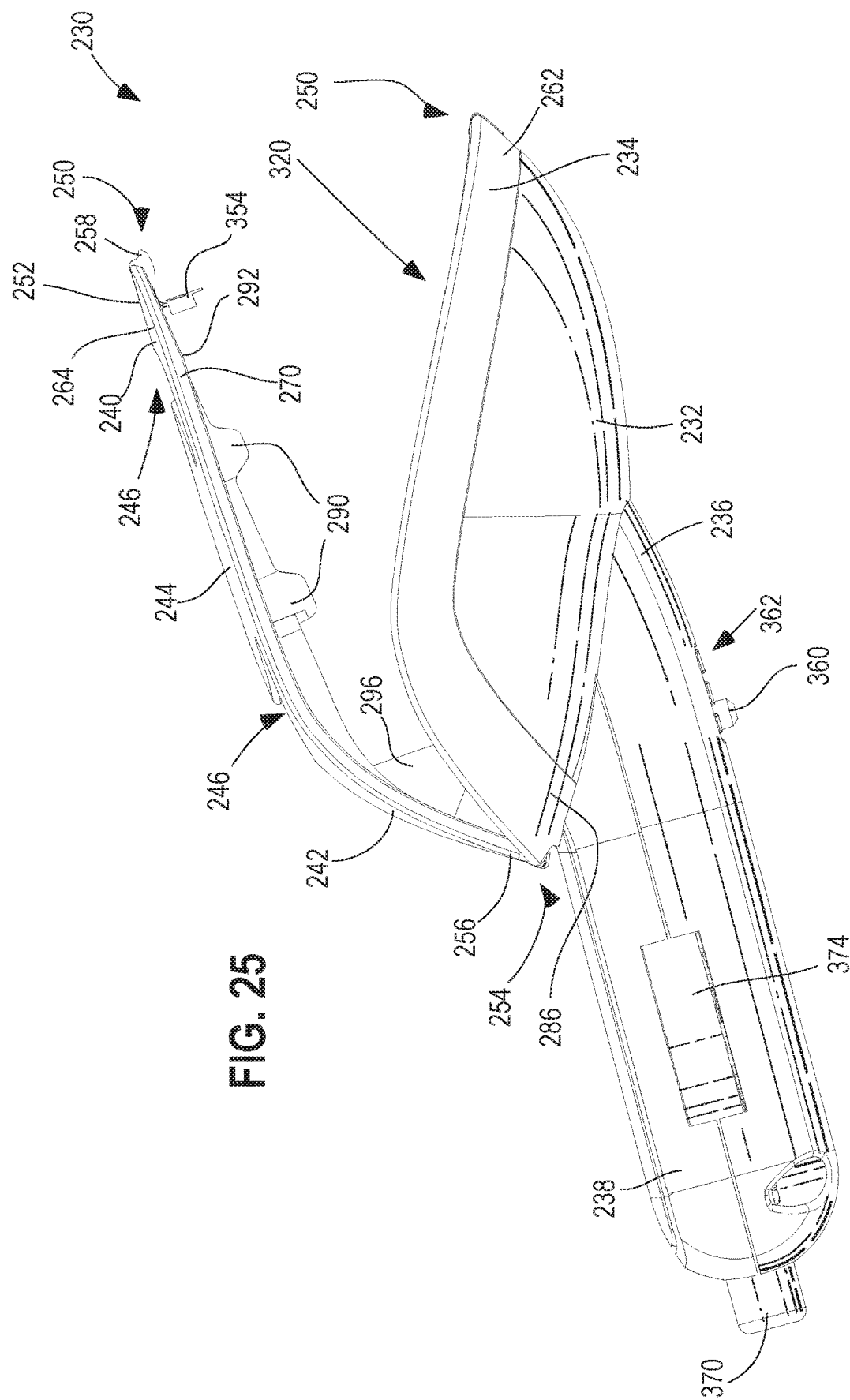
FIG. 25 is a side elevational view of the dispenser of FIG. 17 with the lid in an open configuration.

Referring to FIGS. 20 and 23-25, a plurality of legs 290 is shown that extend downward from a bottom face 292 of the lid 240. The plurality of legs 290 define rails that extend from the bottom face 292 of the lid 240. Referring specifically to FIGS. 23-25, the plurality of legs 290 include two of the legs 290, i.e., a first leg and a second leg, disposed on a first side of the axis M' and two of the legs 290, i.e., a third leg and a fourth leg, disposed on a second side of the axis M', opposite the first side. Further shown in FIG. 20 is a plurality of arms 294 that extend from the inner wall 274 of the top portion 234 of the housing 232. As will be described in greater detail hereinafter below, the arms 294 and distal ends of the legs 290 interface with portions of the cartridge 276 to hold the cartridge in place during use of the dispenser 230. Further, an actuator 296 (FIGS. 21 and 23) is shown that extends from the bottom face 292 of the lid 240. The actuator 296 interfaces with a toggle switch 298 (see FIG. 21) that allows the dispenser 230 to be turned on. As illustrated in FIG. 21, when the lid 240 is in a closed configuration, the actuator 296 engages with the toggle switch 298 to close a circuit, thereby allowing power to flow through the dispenser 230.

In some embodiments, the toggle switch 298 has only two settings, "on" and "off", where the "on" setting is only operable when the lid 240 is in a closed configuration. In other embodiments, additional elements may be added that prevent use of the dispenser 230 unless the dispenser 230 is in a closed configuration, as shown in FIG. 17. Alternatively, the actuator 296 and/or the toggle switch 298 may not be included.

Turning to FIG. 20, a heater comprises a heater element 310 and a substrate 312, which are provided within a receptacle 314. In some embodiments, the heater element 310 may include a resistive heating wire, a conductive silicone heater, a PTC heater, a ceramic heating element, or another heater known to those of skill in the art. In some embodiments, one or more of aluminum, brass, carbon, constantan, copper, iron, manganin, molybdenum, nichrome, nickel, platinum, stainless steel, steel, or zinc may be included within the heater element 310. It is contemplated that the heater element 310 (and/or substrate 312) is in thermal communication with the cartridge 276, either directly or indirectly. It is also contemplated that the heater element 310 (and/or substrate 312) may be in direct contact with the cartridge 276 in some embodiments.

In a preferred embodiment, the heater element 310 comprises one or more resistive heating wires comprising an alloy such as FeCr, FeCrAL, FeCrAlY, NiCr, NiCrFe, NiAl, NiFe, and/or CuNi. The heater element 310 may comprise one or more wires having a diameter of between about 0.2 mm and about 3 mm, or between about 0.5 mm and about 2 mm, or about 1.5 mm. The heater element 310 may also comprise high-resistivity iron-chromium-aluminum alloys, high-resistivity nickel-chromium alloys, low-resistivity nickel-iron alloys, and medium and/or low-resistivity copper-nickel alloys.

As noted above, the heater element 310 may comprise or be combined with a piece of metal or other thermally conductive substrate 312. Such substrates may be formed to partially or entirely surround the heater element 310. In some embodiments the substrate 312 may be a generally flat material, or may be imparted with some curvature. In embodiments that use resistive wires, the heater element 310 may comprise one or more wires that may be woven, may be formed in a cross-hatched pattern, or may be formed in a generally parallel configuration. It is also contemplated that such resistive wires may similarly be formed to be partially or entirely surrounded by a substrate that may take on any geometric shape, e.g., a rectangular element that is thermally conductive. The heater element 310 (and/or substrate 312) may also have a shape that encourages a controlled deformation of the cartridge 276 when the cartridge is subject to a certain amount of heat.

In the embodiments illustrated in FIGS. 17-30, the hinge 254 is located in proximity to the rear end 286 of the top portion 234 of the housing 232. A path of rotation 316 is generally depicted for movement about axis B, as shown in FIG. 23. The path of rotation 316 includes an arcuate length of about 10 cm to about 100 cm. As shown in FIG. 25, when the lid 240 is in an open configuration, a gap 318 (FIG. 23) is formed. It is envisioned that different lengths may be possible, however, it is preferred that the lid 240 be rotatably opened to a degree sufficient to allow for insertion of the cartridge 276. As previously noted, different types of hinges and other connecting means to connect lid 240 to the top portion 234 are also contemplated as are known to those skilled in the art.

Referring to FIG. 20, the top portion 234 is shown provided with a cavity 320. The cavity 320 includes the receptacle 312. In the present embodiment, the cavity 320 is bounded by the inner wall 274 of the top portion 234 and the bottom face 292 of the lid 240. Defined within the inner wall 274 of the top portion 234 is the receptacle 312, which receives the cartridge 276. The receptacle 312 is bounded, in part, by a receptacle wall 322 and a receptacle floor 324 (see FIG. 24). As further illustrated in FIG. 20, the heater element 310 and substrate 312 are provided within the receptacle 314. In the illustrated embodiment, the substrate 312 is adjacent and substantially parallel with the receptacle floor 324 and has a rectangular shape. However, in alternative embodiments the substrate 312 (and/or heater element 310) may comprise different shapes or orientations.

Figure 20A:
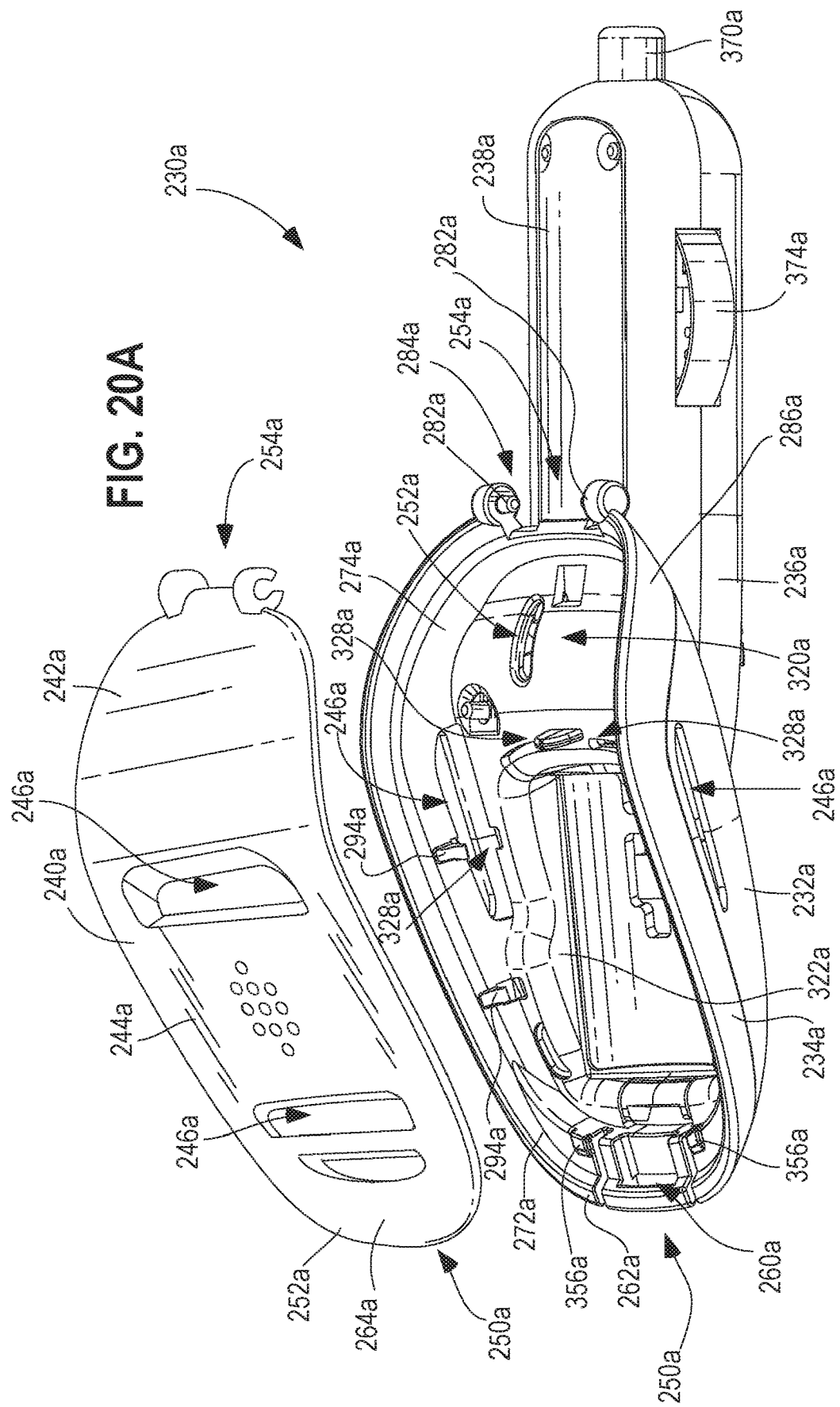
FIG. 20A is a partial, exploded, top right isometric view of a different dispenser to the one shown in FIG. 20 with a lid shown separately and with a cartridge and heater element removed.

Referring to FIG. 20A, a different embodiment of a dispenser 230a is shown, with like structure to that disclosed in connection with the dispenser 230 provided with identical reference numerals. In the present embodiment additional apertures 246a along the bottom portion 236a of the housing 232a are provided. Further, the LED (not shown) is attached directly to the electrical components housed within the plug portion 238a, and the light that illuminates therefrom is directed through one or more light apertures 328a. The light apertures 328a allow light from the one or more LEDs to enter into the cavity 320a and the cartridge 276. In some embodiments, portions of the cartridge 276 act as a waveguide to trap light therein to create an illuminating effect. It is also contemplated that the light that enters the cartridge 276 may be used to provide a use-up cue function for a user to determine how much of a volatile is remaining in the cartridge. For example, in some embodiments, a fully filled cartridge 276 may contain a volatile or volatile carrier that has a color such as purple, red, green, yellow, blue, etc. When the colored volatile or carrier is subject to light from the LED, an ambient glow is apparent to a user. As the volatile within the cartridge 276 diminishes due to the emanation thereof, the light illuminating through the cartridge 276 will, over time, turn to white. In a preferred embodiment, the one or more LEDs are surface mounted to a printed circuit board, and are mounted in a location that allow them to illuminate the cartridge 276.

Figure 22:
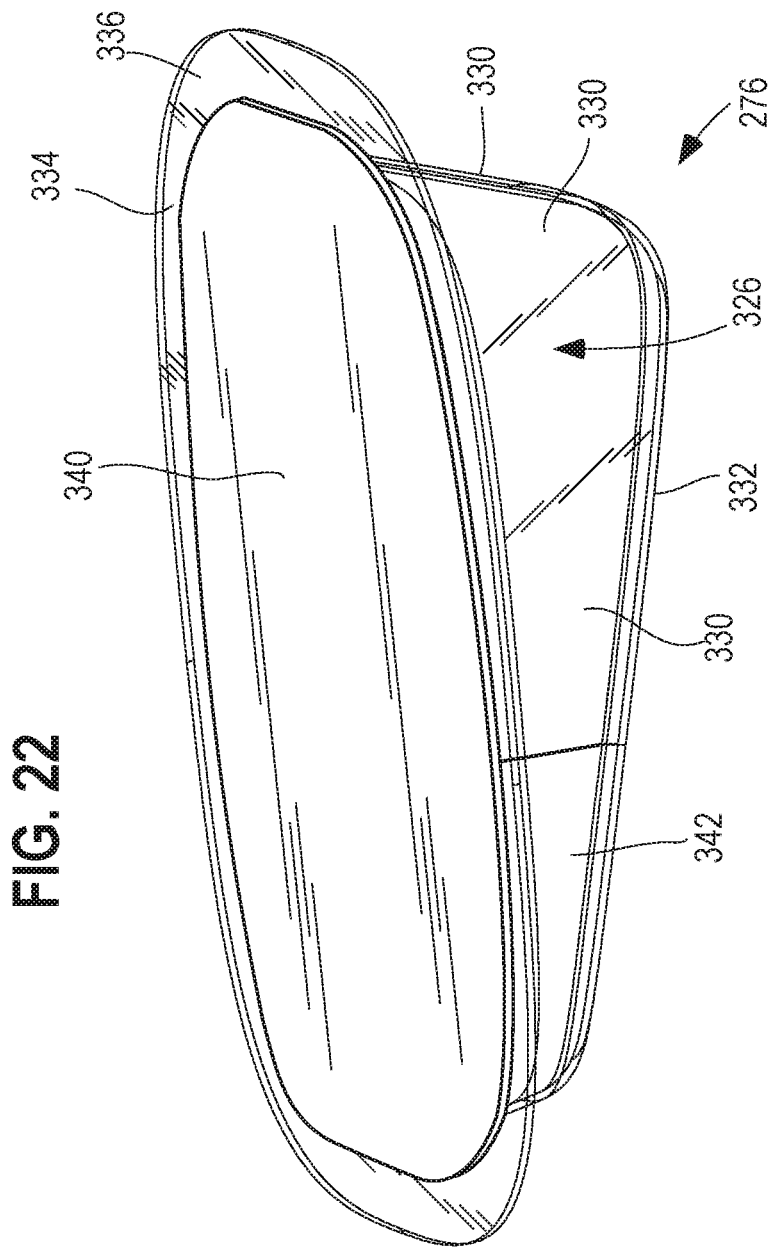
FIG. 22 is a top right isometric view of another cartridge for use with the dispensers disclosed herein.

Turning now to FIG. 22, one exemplary embodiment of the cartridge 276 for use with the dispenser 230 is shown. The cartridge 276 includes the reservoir 326, which is defined by a sidewall 330 and a bottom wall 332. In the present embodiment, the sidewall 330 may be generally characterized as having first, second, third, and fourth walls with curved edges. The sidewall 330 may be perpendicular with the bottom wall 332 or may be inclined relative thereto. In the present embodiment, an upper end 334 of the sidewall 330 terminates at a flange 336, which extends peripherally thereabout. The flange 336 preferably has a uniform thickness and may extend radially outward from the upper end 334 so that a width of the flange 336 is uniform thereabout. Numerous features, as discussed below, may be provided about or below the flange 336 to facilitate airflow along portions of the cartridge 276, to provide rigidity to the cartridge 276, or for some other reason. For example, deformations, apertures, protrusions, or material added to the cartridge 276 may be provided to add rigidity thereto, or allow for a controlled change in the shape of the cartridge 276, such as a controlled collapse of the sidewall 330 and/or bottom wall 332.

Turning now to FIGS. 22A and 22B, alternative embodiments of a cartridge 276a, 276b, respectively, for use with the dispenser 230 are shown. The cartridges 276a, 276b include reservoirs 326a, 326b, which are defined by sidewalls 330a, 330b and bottom walls 332a, 332b, respectively. The sidewalls 330a, 330b may be perpendicular with the bottom walls 332a, 332b or may be inclined relative thereto. In the present embodiments, upper ends 334a, 334b of the sidewalls 330a, 330b terminate at flanges 336a, 336b, respectively, which extend peripherally thereabout. The flanges 336a, 336b preferably have a uniform thickness and may extend radially outward from the upper ends 334a, 334b so that a width of the flanges 336a, 336b are uniform thereabout. A plurality of ridges or rigidity features 344a, 344b may be provided along the sidewalls 330a, 330b, respectively, to provide for a rigid, non-collapsible cartridge. Alternatively, the ridges 344a, 344b may be included to allow for a limited collapse of the cartridges 276a, 276b and/or to allow for a controlled collapse of the cartridges based on user preferences. Such features may be of particular relevance upon the application of heat to the cartridges 276a, 276b, since the sidewalls 330a, 330b and/or bottom walls 332a, 332b may change shape or deform.

The ridges 344a, 344b may prevent collapsing, or allow for controlled collapsing of the sidewalls 330a, 330b. In some forms, the collapsing of the sidewalls 330a, 330b may be controlled to provide a use-up cue function for users of the dispenser 230. The ridges 344a have a generally triangular configuration and the ridges 344b have a generally square configuration; however, any geometric shape is envisioned including, but not limited to, rectangles, curvilinear forms, half circles, trapezoids, ellipses, pentagons, octagons, any other suitable shape, or any combination of the foregoing shapes. It is also envisioned that the ridges 344a, 344b may have an aesthetic component that may be desired by users apart from any functionality. The ridges 344a, 344b may be disposed adjacent one another, or portions of the planar sidewall 330a, 330b may be provided therebetween.

Referring to FIG. 22, the cartridge 276 further includes a permeable membrane 340 that isolates the reservoir 326. More particularly, the permeable membrane 340 is attached to portions of the flange 336 to allow for diffusion of a volatile material 342 therethrough during use of the cartridge 276. It is also anticipated that a removable impermeable laminate (not shown) may be provided prior to activation of the cartridge 276, which extends over the permeable membrane to prevent diffusion of the volatile material.

In a preferred embodiment, the cartridge 276 is heated by ambient heat of the surrounding atmosphere in a non-use or non-operational state of the dispenser. In a preferred embodiment, the volatile material 342 and/or a carrier liquid disposed within the cartridge 276 evaporates or emanates into the surrounding atmosphere when the surrounding temperature is above about 10° C., or above about 15° C., or above about 20° C., or above about 25° C. In some embodiments, the volatile material 342 may emanate at a temperature of about 10° C., or about 15° C., or about 20° C., or about 25° C.

Referring to FIGS. 20 and 21, the cartridge 276 is sized to fit within the receptacle 314 of the cavity 320. When inserted, the receptacle wall 322 receives and is adjacent to the sidewalls 330 of the cartridge 276. The flange 336 of the cartridge 276 is seated beneath the arms 294 of the housing 232 and is in contact with the legs 290 of the lid 240 when the lid is in a closed position. Thus, the cartridge 276 nests within the receptacle 314 and is held in place with retaining features that include the receptacle wall 322, the legs 290, and the arms 294. Referring to FIGS. 19, 20, and 24, the heater element 310 is positioned between the receptacle floor 324 and the bottom wall 332 of the cartridge 276. Thus, during use of the dispenser 230, the flange 336 of the cartridge 276 is held securely in place by the arms 294 and the legs 290, the sidewalls 330 of the cartridge 276 snugly nest against the receptacle wall 322, and the bottom wall 332 of the cartridge is juxtaposed with the heater element 310 (and/or substrate 312), which is adjacent the receptacle floor 324 within the receptacle 314. However, in some embodiments, some portions of the cartridge 276, including the flange 336, the sidewalls 330, and/or the bottom wall 332 may not be juxtaposed or adjacent one or more portions of the housing 232 or the heater. In a preferred embodiment, no portion of the lid 240 is in contact with any portion of the cartridge 276, thus, a space or a head space exists between the permeable membrane 340 of the cartridge and the bottom face 292 of the lid 240. In a preferred embodiment, one or more support structures in addition to the arms 294 support the flange 336, the sidewall 330, and/or the bottom wall 332 to provide for a secure retention of the cartridge 276 within the housing 232. In some embodiments, the dispenser 230 need not include any of the legs 290, the arms 294, or any other support structure.

When the dispenser 230 is provided in a closed state, e.g., as shown in FIGS. 17, 18, and 21, the actuator 296 engages the toggle switch 298 to close the circuit, as will be discussed below. While the cartridge 72 described above may allow for no, or substantially no, diffusion of the volatile through the permeable membrane 94, the dispenser 230 is partially sealed to allow for some diffusion of the volatile through the permeable membrane 340 when the dispenser 230 is in either an active or an inactive state. Such an inactive state, i.e., a non-use or non-operational state, of the dispenser 230 may be characterized as any time after the impermeable membrane has been removed from the cartridge 276, the cartridge 276 is disposed within the receptacle 312, and the dispenser 230 itself is not emanating heat.

The partial seal is created by the inclusion of one or more of the apertures 246 within the lid 240. In some embodiments, the apertures 246 may also be provided along the top portion 234 or the bottom portion 236 of the housing 232, or both. Such a partial seal allows for some volatile emission from the dispenser 230 when the dispenser is no longer powered or in an otherwise operational state. Allowing for some diffusion of the volatile material through the permeable membrane 340 and out to the surrounding atmosphere provides for ambient diffusion of the material in some circumstances where a user may not intend to completely shut off the dispenser 230 when power is not provided thereto. Further, allowing some of the volatile to diffuse out of the device may further prevent the condensation (or buildup) of the dispensed material within the dispenser 230 during a non-use or non-operational state. The dispensed material may broadly encompass any component provided within the reservoir 326 of the cartridge 276, including the volatile material, that is emanated through the permeable membrane, e.g., a carrier material.

Referring again to FIG. 22, the reservoir 326 may be filled with an active ingredient or volatile material comprising one or more components as described above. In some embodiments, the reservoir 326 is made of one or more of the materials as discussed above with respect to the reservoir 84. In alternative embodiments, the lid 240 is made of transparent materials so that a user can easily determine when to replace an empty reservoir. In some embodiments, the lid 240 includes a transparent window (not shown) to provide access for a user to view an empty reservoir and determine whether to refill the dispenser 230. In one embodiment, the lid 240 is opaque.

Figure 24A:
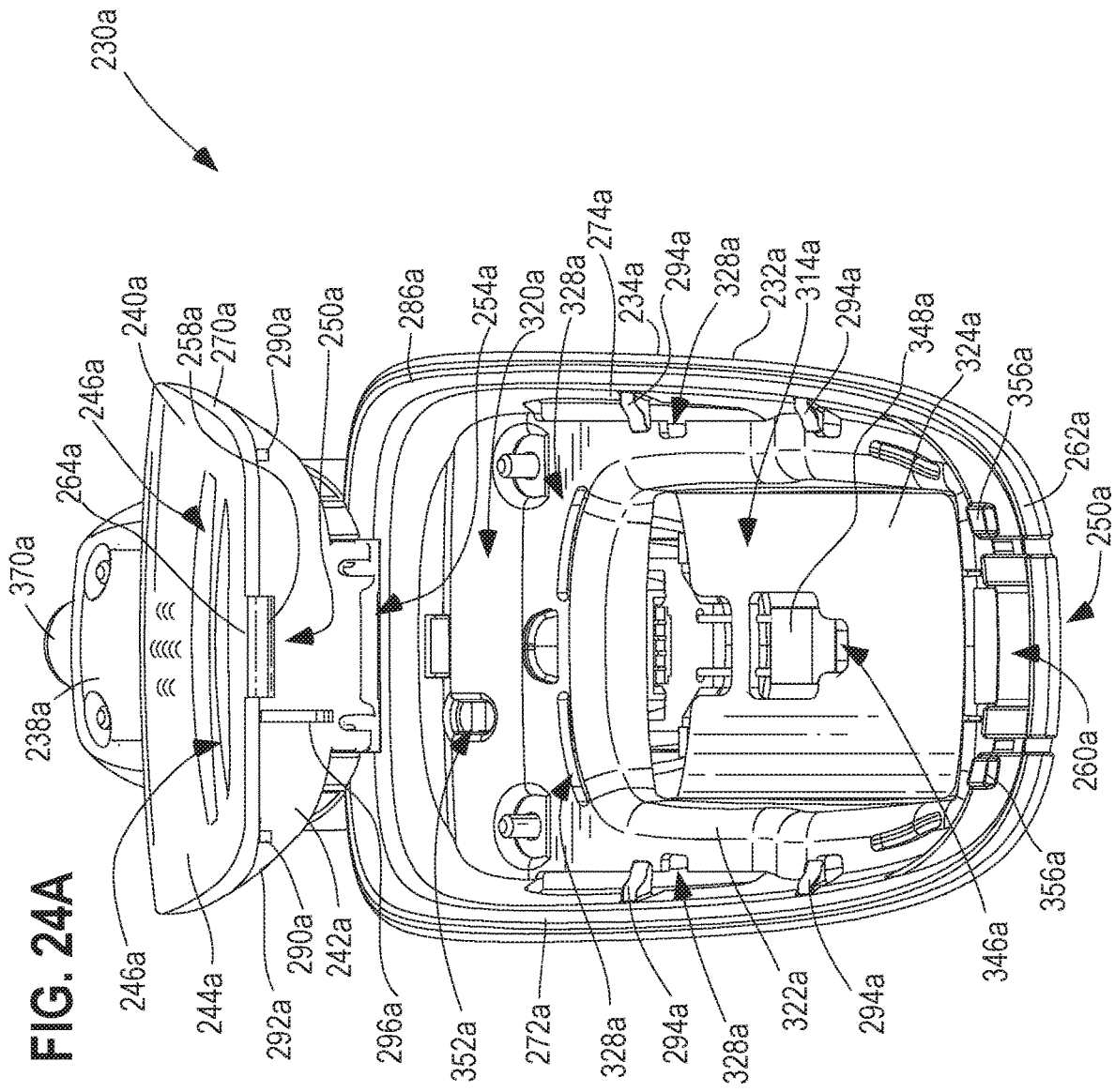
FIG. 24A is a top plan view of the dispenser of FIG. 20A with the lid in an open configuration with a cartridge and a heater element removed for clarity.

Referring to FIG. 24, the dispenser 230 is shown without the cartridge 276 and the heater element 310. A floor aperture 346 is provided within the receptacle floor 324. The floor aperture 346 may be included to allow heat to dissipate through the receptacle floor 324 and out of the housing. Referring to FIG. 24A, a thermal switch or fuse 348a may be provided beneath or adjacent the floor aperture 346a. In some embodiments, surfaces adjacent the floor aperture 346 put back pressure on a thermal cut-off (TCO), as discussed below with respect to FIG. 24A, to keep the TCO in contact with the heater. Also shown in FIG. 24 is a light or a light emitting diode (LED) 350 and an actuator aperture 352. The actuator aperture 352 is provided within a portion of the inner wall 274, and is shaped to receive the actuator 296 when the dispenser 230 is in a closed position. Additionally, FIGS. 24 and 25 depict two supports 354, which protrude downward from the bottom face 292 of the lid 240. The supports 354 interface with a plurality of projections 356, which are formed within the top portion 234 of the housing 232. The supports 354 provide further support for the lid 240 when the lid is in the closed position.

Still referring to FIG. 24, a plurality of posts 358 are illustrated within the floor aperture 346. In a preferred embodiment, the posts 358 receive the thermal switch or fuse 348a (see FIG. 24A). As discussed above, and referring to FIG. 24A, the fuse 348a may be a thermal switch that opens at a high temperature, possibly with an audible sound, and re-closes when the temperature drops back down to a threshold level. The fuse 348a may comprise a bimetallic strip, a bimetallic dome-shaped cap which "clicks" to an inside-out inverted cap shape when heated, or some other component. In a preferred embodiment, the fuse 348a is reusable and is suited to protecting against temporary heat increases within the housing 232. In some embodiments, the fuse 348a is a Eutectic TCO. In other embodiments, the fuse 348a is a positive temperature coefficient thermistor that has a "switch" temperature at which the resistance suddenly rises rapidly, limiting the current through the circuit. When used in conjunction with a thermistor relay, the PTC thermistor may switch off the electrical system at a desired temperature. As discussed above with respect to the dispenser 30, one or more thermistors may be provided along any part of the device that can cause the electrical system, or some components of the electrical system, to be shut off when a threshold temperature is reached.

Figure 26:
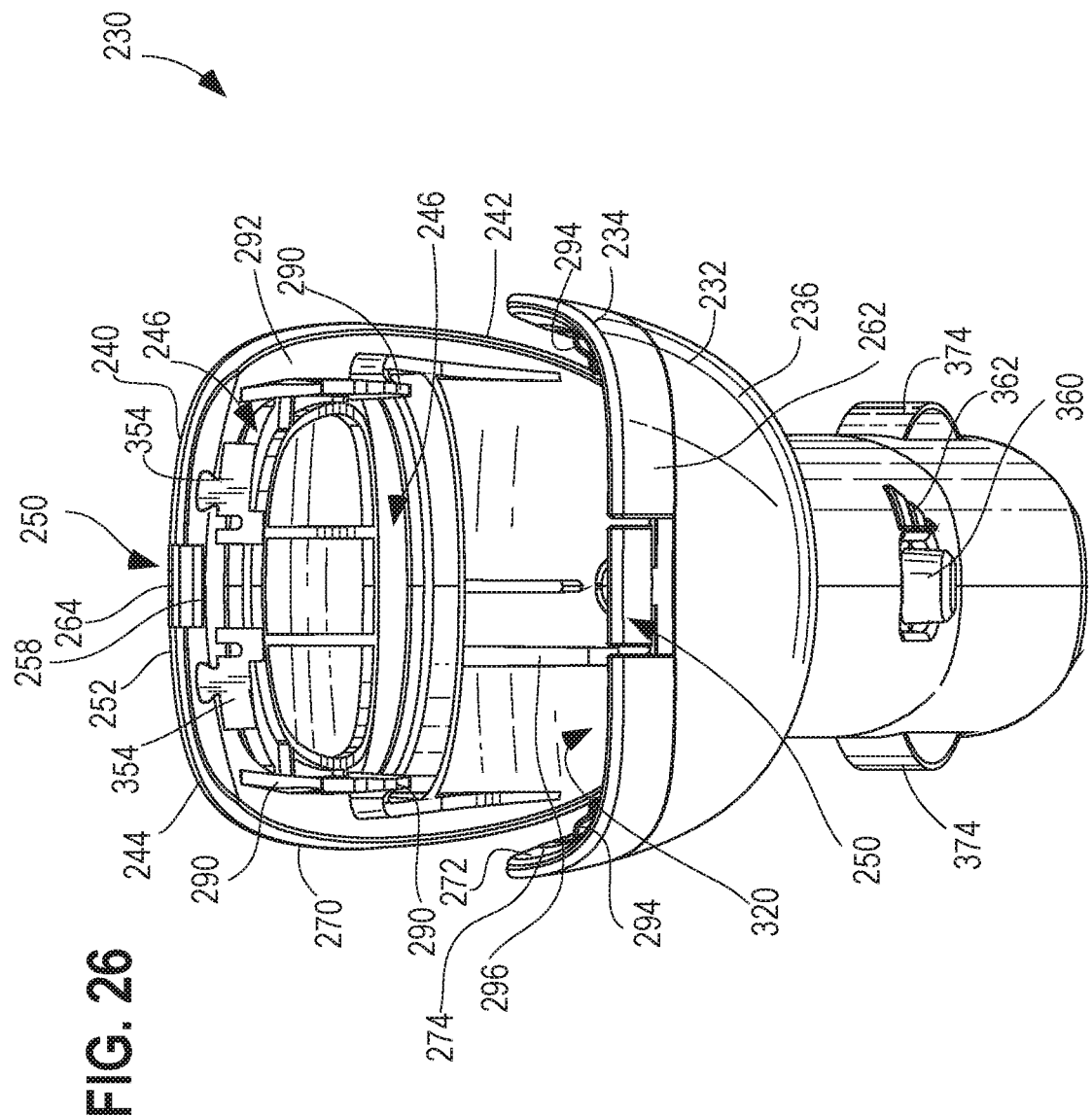
FIG. 26 is a front elevational view of the dispenser of FIG. 17 with the lid in an open configuration.
Figure 27:
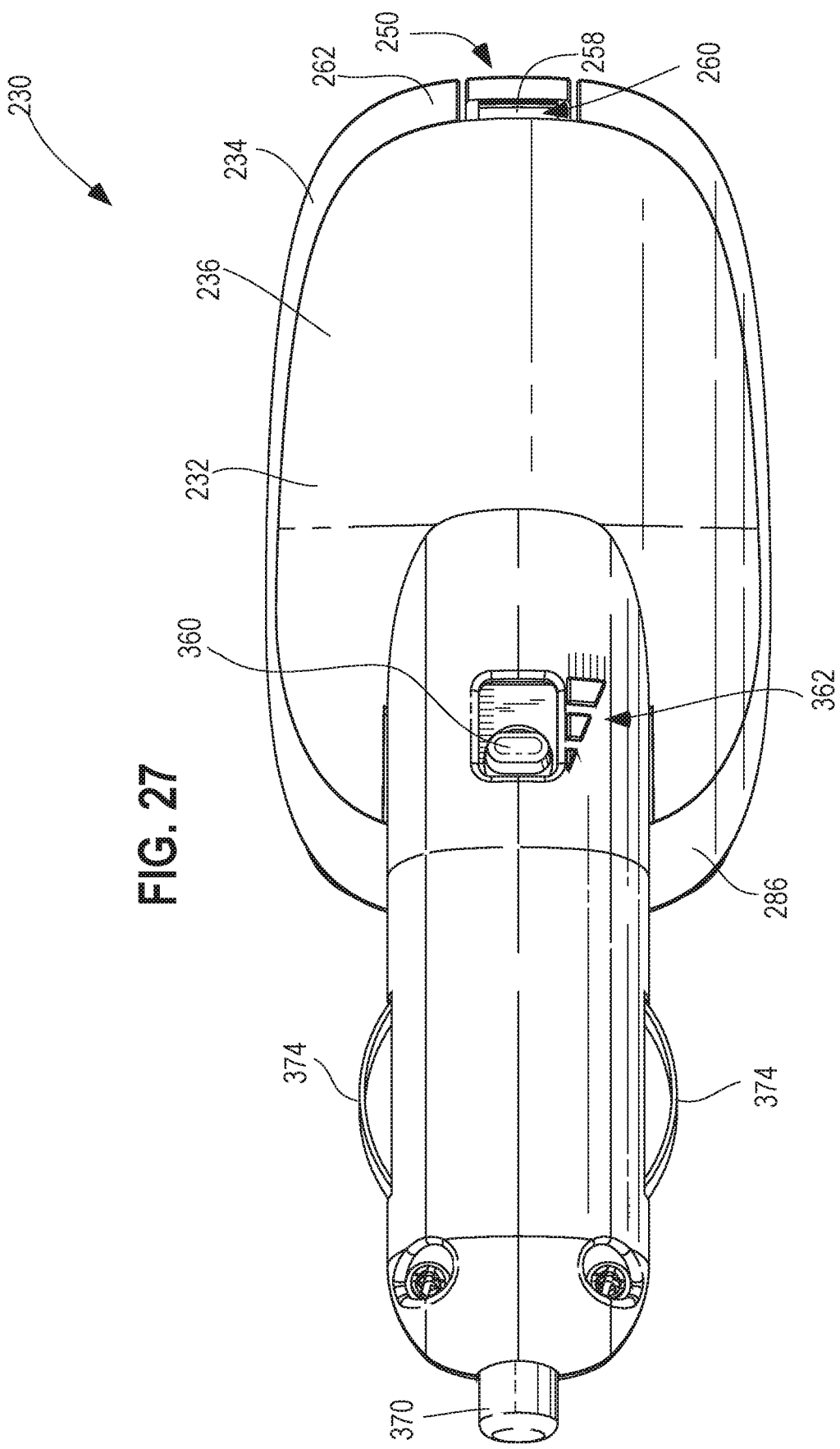
FIG. 27 is a bottom plan view of the dispenser of FIG. 17.

Referring to FIGS. 26 and 27, the bottom portion 236 of the housing 232 is shown to include a power switch 360 that is operable to manipulate the dispenser 230 between an "off" configuration and one or more "on" configurations. Shown adjacent the power switch 360 are power gradations 362 that indicate to a user the power that will be provided to the dispenser 230 depending on the location of the power switch 360. In some embodiments, the power switch 360 is operable to manipulate the dispenser 230 between an "off" position, a "low" position, a "medium" position, and a "high" position. Each of the "on" configurations, e.g., "low," "medium," and "high," may provide for a differing amount of power supplied to the heater element 310, which can alter the amount of volatile that is released from the cartridge 276. In some embodiments, the power switch 360 is in the form of a knob, a dial, a button, or a lever.

Figure 28:
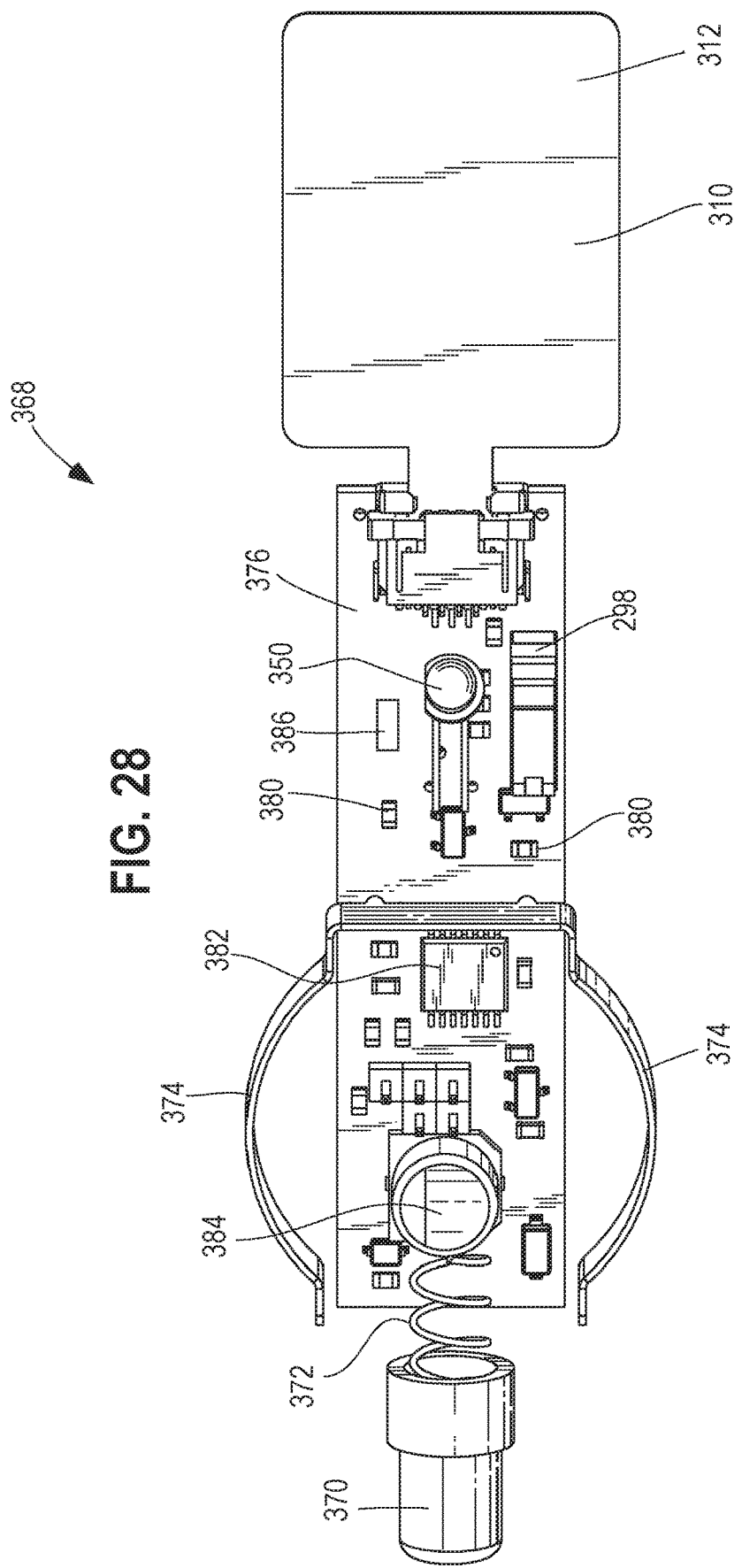
FIG. 28 is a is a top plan view of an electrical assembly for use with any of the dispensers disclosed herein.

Referring to FIGS. 28-30, the electrical portion of the dispenser 230 will be described with greater particularity. Specifically with reference to FIG. 28, a heater assembly 368 comprising a portion or all of the electrical components of the dispenser 230, is shown. The heater assembly 368 includes a positive contact 370 configured to deliver power to the heater assembly 368 by coupling to and making an electrical contact with a power source contact from a vehicle (not shown), e.g., a lighter socket, or other power source outlet. FIG. 28 also depicts a positive post 372 and a common contact 374, which are connected to a printed circuit board (PCB) 376, where the PCB 376 includes a number of electrical components controlling the operation of the heater assembly 368.

FIG. 28 illustrates that the PCB 376 is coupled with the heater element 310, which may comprise one or more separate heater elements and substrates. In the present embodiment the heater element 310 comprises a single heating element, e.g., a single, thin piece of material, at least a portion of which comprises heat conductive material as described above. The PCB 376 also includes a plurality of LED resistors 380 corresponding to the LED 350. Further, the PCB 376 includes a microcontroller 382 and a voltage regulator 384. The toggle switch 298 is also shown adjacent the LED 350.

In a preferred embodiment, the electrical assembly of the dispenser 230 is provided with the power switch 360 for turning the dispenser 230 between "off" and "on" states, which may include at least two active operational settings as discussed above. In some embodiments, the operational states include an infinite number of "on" states that are achieved depending on how far the power switch 360 has been adjusted by a user. In other embodiments, the dispenser 230 is always in an "on" or operational state and the power switch 360 provides for the variation of two or more operational settings. In the present embodiment, the power switch 360 is a slide switch movable between an off position, a first operational position, a second operational position, and a third operational position (see FIG. 27).

When the power switch 360 is moved to the off position, electric power cannot flow from a power source to components on the PCB 376. Further, when the lid 240 is in an open configuration (see FIG. 25), the toggle switch 298 is in the "off" position, thus, power cannot be provided to the heater element 310. As such, none of the LEDs transmit light when either the power switch 360 or the toggle switch 298 is in the "off" position. When both the toggle switch 298 and the power switch 360 are moved to the "on" position and one of the operational positions, respectively, power flows from the power source through the positive post 372 to the PCB 376. In a particular embodiment, the provision of power results in the LED 350 emitting a light, which may be a green light, or a light having any other color. In certain embodiments, the flow of power from the positive post 372 to the heater element 310 is controlled by a transistor as discussed above with respect to the dispenser 30.

Still referring to FIG. 28, an optional vibration sensor 386 is shown that is configured to detect vibrations. In some embodiments, the vibration sensor 386 is operable to provide information to the microcontroller 382 regarding whether the vehicle within which the dispenser 230 is disposed is, in fact, turned on and is running. By detecting such vibrations, the vibration sensor 386 may provide vibration information to the microcontroller 282, and the microcontroller 382 may prevent power from being sent to the electronic components of the dispenser 230. Thus, the dispenser 230 may turn off when the vehicle is in an off state, regardless of whether power is still being provided to the positive post 370. In some embodiments, a timer (not shown) is coupled with the microcontroller 382 that allows the microcontroller 382 to shut off the electronic components a specified amount of time after the vibration sensor 386 has ceased receiving vibration information indicating that the vehicle is turned "on". This function preserves vehicle battery life for vehicles with power outlets that remain powered "on" when the ignition switch is turned off. The vibration sensor 386 may comprise an accelerometer, a gyroscope, or another acceleration detecting component.

Referring again to FIG. 23, the heater element 310 is disposed within the receptacle 314, adjacent to where the cartridge 276 is seated. As similarly discussed with respect to the dispenser 30 above, portions of the PCB 376 including the heater element 310 are provided within the bottom portion 236 and the plug portion 238 of the housing 232. Preferably, the heater element 310 (and/or substrate 312) is provided entirely below the bottom wall 332 of the reservoir 326 of the cartridge 276. In one particular embodiment, a surface area of the bottom wall 332 is greater than a combined surface area of the heater element 310 (or substrate 312) and defines a boundary within which the heater element 310 resides to provide for effective heat transfer, i.e., the heater element 310 (or substrate 312) is below the cartridge 276 and does not extend beyond a perimeter of the bottom wall 332. In other embodiments, the heater element 310 (or substrate 312) extends beyond a perimeter of the bottom wall 332 and/or includes heater elements adjacent the sidewall 330. In some embodiments, the cartridge 276 deforms in some fashion due to the heat transferred thereto by the heater element 310. In certain embodiments, the various heating profiles of the heater element 310 may be regulated by any of the means as discussed above with respect to the dispenser 30.

Turning to FIG. 31, one aspect of a heater element 310a for use in the dispenser 230 is depicted. In this example, the substrate 312 is generally rectangular with a length K and a width W when viewed from above, although the substrate 312 may be of any shape, e.g., in order to conform to the area in the dispenser 230 in which it is to be located, or in order to conform to a shape of receptacle floor 324. It also will be appreciated that the substrate 312 may be flat or have a curvature or other variation to its depth, as described above.

A resistive wire 420 is disposed on or embedded in the substrate 312 in a pattern that provides diffuse, generally even heating throughout the substrate 312. For example, the wire 420 may have a serpentine, zig-zag, or other arrangement, in which the wire 420 alternates directions across the substrate 312. In the specific example of FIG. 31, the wire 420 first enters or couples to the substrate 312 at a location approximately half-way along the width W of the substrate 312. The wire 420 then proceeds in a direction parallel to the length K of the substrate 312 to a location approximately half-way across the length K of the substrate 312 before reversing direction, proceeding back toward an edge 422 of the substrate 312, and then reversing direction again. The wire 420 continues this alternating pattern until it is disposed proximate an upper edge 424, at which point it extends across substantially the entire length of the substrate 312. In this example, the wire 420 includes an inwardly-depending section 426 approximately half-way across the length K of the substrate 312, although other variations may not include this section 426. Upon reaching an edge 428 opposite from where the wire 420 first enters or couples to the substrate 312, the wire 420 again may reverse direction and continue its snaking pattern back down the width W of the substrate 312. The wire 420 may continue to follow an alternating path around the substrate 312, such that the heater element 310 may be substantially symmetrical about a line bisecting its width.

As seen in FIG. 31, the wire 420 has a substantially constant width along its length. The spacing between portions of the wire 420 also is substantially constant throughout the substrate, e.g., approximately equal to the width of the wire 420. As a result, the heater element 310 may deliver substantially even heating along its surface. In another aspect, portions of the wire 420 may be spaced closer or farther apart, thereby creating localized areas of more or less intense heating, respectively. As discussed above, the layout depicted in FIG. 31 may only be exemplary, and the exact layout of the wire 420 on or within the substrate 312 may be subject to modification. As shown in FIG. 31A, a thermistor 440 may be included that is integral with the substrate 312 and the wire 420. The thermistor 440 may be operable to provide feedback to the controller 382 indicative of a temperature of the heater element 310a.

Figure 32:
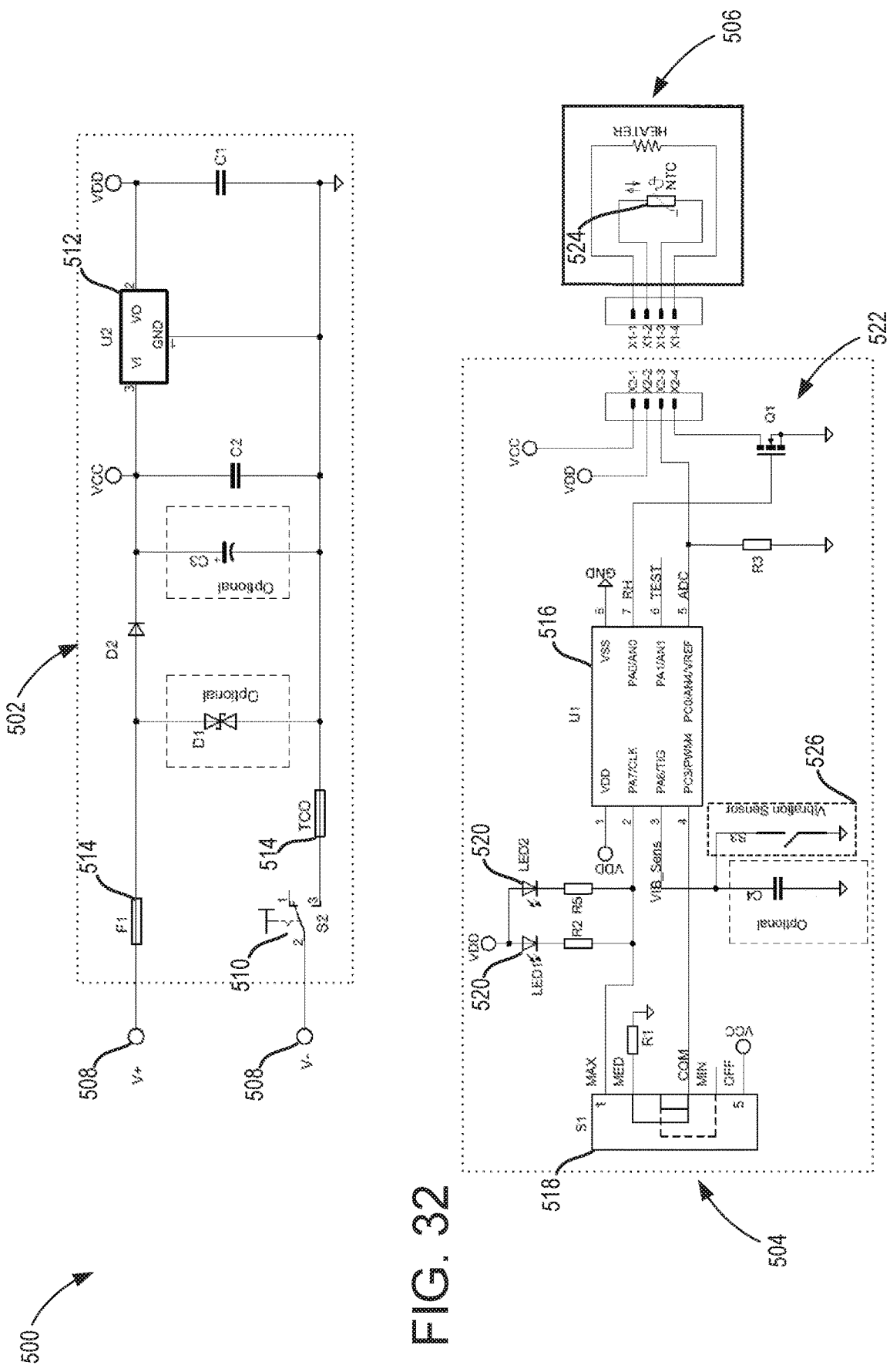
FIG. 32 is an electrical schematic of one embodiment of a heater assembly.

Referring now to FIG. 32, a schematic diagram illustrating an electrical assembly 500 of a heater assembly for use in a volatile dispenser, in accordance with aspects of the present disclosure, is shown. The electrical assembly 500 includes a power stage 502, a controller stage 504, and a heating element 506. In particular, the power stage 502 is configured to receive power from a power source, such as a car lighter socket or other source, by way of input contacts 508, and manage the received power to operate various electrical components of the electrical assembly 500, including energizing the heating element 506. As shown in FIG. 32, the power stage 502 may include a toggle switch 510 having an "on" and an "off" position, for example, and a voltage regulator 512. The power stage 502 may also include a number of other electrical components, including capacitors, resistors, inductors, diodes, and so forth. In addition, as shown in FIG. 32, the power stage 502 may also include a number of fuses 514, such as electrical and thermal fuses, for protecting circuit components of the electrical assembly 500 in case of electrical or thermal spikes, transients, or overload.

Still referring to FIG. 32, the control stage 504 includes a microcontroller unit (MCU) 516 programmed to control the operation of the heating element 506, and other electrical components. In addition, the control stage 504 also includes a power switch 518 for selecting the mode of operation. Specifically, the power switch 518 activates inputs to the MCU 516 to indicate a target temperature for the heating element 506. By way of example, the power switch 518 may include an "off" position, and a number of "on" positions, such as a "low," "medium," and "high" position. The position of the power switch 518 may be indicated by LEDs 520 included in the control stage 504 circuitry, as shown in FIG. 32.

When the toggle switch 510 and power switch 518 are activated to an "on" position, the MCU 516 can direct electric current to flow to the heating element 506, using activation circuitry 522 and power supplied by the power stage 502. Once the target temperature associated with the power switch 518 setting is reached, the MCU 516 can cut off the electrical current supplied to the heating element 506 while continuously monitoring the temperature of the heating element 506 using signals provided by thermistor 524 arranged on or in proximity to the heating element 506, as shown in FIG. 32. When the temperature drops to a predetermined value, the MCU 516 may then restore electrical current once again. In some aspects, a PWM algorithm may be used to allow the heating element 506 to heat up quickly, which in turn would allow a faster fragrance or volatile release.

In some implementations, the MCU 516 may also be programmed such that if the power switch 518 is inadvertently moved to an intermediate position, that is a position between allowable settings, as described above, the electrical assembly 500, or portions thereof, may be disabled, to avoid unpredictable behavior.

As shown in FIG. 32, the control stage 504 may include an optional vibration sensor 526 configured to detect vibrations in the electrical assembly 500 and affect operation of the heating element 506, as well as other electrical components. In one example, the vibration sensor 526 may indicate whether a vehicle is in operation by sensing the vibration of an engine. In another example, the vibration sensor 526 may detect a movement of the volatile dispenser. In some implementations, the vibration sensor 526 may comprise an accelerometer, a gyroscope, or another acceleration detecting component. In detecting vibrations, or lack thereof, the vibration sensor 526 may, for example, open or close a current pathway that is detectable by the MCU 516. In turn, the MCU 516 may then allow or prevent power being provided to the heating element 506. For example, MCU 516 may de-energize the heating element 506 when a vehicle is off.

In some embodiments, a timer may also be coupled to the MCU 516, allowing the MCU 516 to shut off specific electronic components for a predetermined amount of time after the vibration sensor 526 has ceased receiving vibration information. This function may help preserve battery life for vehicles with power outlets that remain powered when the ignition switch is deactivated. Although a particular implementation is shown in FIG. 32 for the power stage 502 and controller stage 504 for managing and controlling power provided to the heating element 506, any number of modifications and variations are possible to provide functionalities as described above, as well as other functionalities. Additionally, the heating element 506 is shown to include a single resistive wire, yet it may be readily appreciated that any variation, such as two or more resistive wires, in accordance with the present disclosure may also be possible. Any of the components described above with respect to the schematic illustrated in FIG. 32 may be the same as, or interchanged with components described above with respect to the heater assembly shown in FIGS. 14, 15, and 28-31A.

Any of the embodiments described herein may be modified to include any of the structures or methodologies disclosed in connection with different embodiments. Any of the components as discussed above may be coupled with any other component by any securement mechanism known to those of ordinary skill in the art, such as screws, rivets, bolts, adhesives, ultrasonic welding, or any other fastener. Further, the present disclosure is not limited to air fresheners for use in automobiles but may apply to any device that releases a volatile material into an atmosphere. The cartridges described herein may have any number of different shapes, and may be filled with any volatile material known to those of ordinary skill in the art. Further, any type of container, including the above described cartridges, may be used with the herein described embodiments, including a bottle, a bottle having a wick, a canister, a refill, or any other vessel for holding a volatile material known to those of ordinary skill in the art. The dispenser may also be powered through any number of alternative power sources, such as, a cord, a USB, a mini-USB, etc.

INDUSTRIAL APPLICABILITY

A dispenser is presented that is controllable between various states to regulate the emission of a volatile material.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:
1. A dispenser, comprising:
a housing defining a central plane and a cavity in which a container is disposed, the housing including;
a receptacle wall that defines a receptacle within the cavity;
a plurality of legs that extend inward from the housing, the plurality of legs comprising at least a first leg, a second leg, a third leg, and a fourth leg; and
a plurality of apertures that are provided to facilitate airflow through the dispenser; and
the container that fits within the receptacle, the container including:
a reservoir containing a volatile material therein, the reservoir comprising a bottom wall and a sidewall;
a flange extending from the sidewall; and an impermeable membrane that encloses the volatile material within the reservoir, wherein the container nests within the receptacle and is held in place with retaining features that include the receptacle wall and the plurality of legs, wherein the impermeable membrane is connected to the flange prior to activation of the container to prevent diffusion of the volatile material, wherein the first leg and the second leg are disposed on a first side of the central plane, and the third leg and the fourth leg are disposed on a second side of the central plane, opposite the first side, and wherein distal ends of the first leg, the second leg, the third leg, and the fourth leg are in direct contact with the flange when the dispenser is in an activated configuration.

2. The dispenser of claim 1, wherein the first leg and the third leg are disposed equidistant from the central plane.

3. The dispenser of claim 2, wherein the flange is held in place by all of the plurality of legs in the activated configuration.

4. The dispenser of claim 1, wherein the housing comprises a top portion and a bottom portion.

5. The dispenser of claim 4, wherein the top portion is received within the bottom portion.

6. The dispenser of claim 5, wherein the receptacle is formed by both the top portion and the bottom portion.

7. The dispenser of claim 5, wherein the plurality of apertures are provided along the top portion and the bottom portion of the housing.

8. The dispenser of claim 1, wherein the housing is configured to be adjusted between an open configuration and a closed configuration.

9. The dispenser of claim 1, wherein a resistive heating wire is provided to heat the container, the resistive heating wire comprising one of FeCrAL, FeCrAlY, NiCr, NiCrFe, NiAl, NiFe, or CuNi.

10. The dispenser of claim 1, wherein the volatile material is provided as one of a liquid, a thickened liquid, or a gel.

11. The dispenser of claim 10, wherein a permeable membrane extends across the reservoir.

12. The dispenser of claim 11, wherein the flange extends outwardly from the sidewall.

13. The dispenser of claim 12, wherein the impermeable membrane extends over the permeable membrane to prevent diffusion of the volatile material.

14. A dispenser, comprising:
a housing defining a central plane and a cavity into which a refill is configured to be inserted, the housing including:
a receptacle wall that defines the cavity within the housing;
a plurality of legs that extend from the housing, the plurality of legs defining rails and comprising at least a first leg, a second leg, a third leg, and a fourth leg; and
one or more apertures that are disposed along an exterior of the housing to facilitate airflow through the dispenser; and
a cartridge defining a reservoir that holds a volatile material, the cartridge provided within a receptacle and including:
the reservoir containing a volatile material, the reservoir defining a bottom wall and a sidewall,
a flange that extends outwardly from the sidewall; and
an impermeable membrane that encloses the volatile material within the reservoir, wherein the cartridge is disposed within the receptacle and is nested against retaining features that include the receptacle wall and the plurality of legs, wherein the volatile material escapes the reservoir when air flows into the reservoir, wherein the first leg and the second leg are disposed on a first side of the central plane, and the third leg and the fourth leg are disposed on a second side of the central plane, opposite the first side, and wherein distal ends of the first leg, the second leg, the third leg, and the fourth leg are in direct contact with the flange when the dispenser is in an activated configuration.

15. The dispenser of claim 14, wherein the one or more apertures that allow air to flow into the housing are disposed within a top portion of the housing.

16. The dispenser of claim 15, further including a heating element that is in electrical communication with an electrical contact.

17. The dispenser of claim 15, wherein the one or more apertures allow air to flow into a bottom portion of the housing, which is coupled with the top portion of the housing.

18. The dispenser of claim 17, wherein the flange is held in place by the plurality of legs.

19. A dispenser, comprising:
a housing defining a central plane and a cavity having a receptacle; and
a cartridge disposed within the receptacle, the cartridge having a reservoir holding a volatile material and an impermeable membrane extending thereacross,
wherein the housing includes a receptacle wall that defines the receptacle, a plurality of legs extend inward from the receptacle wall of the housing, and a plurality of apertures are provided along the housing to allow air to flow into the cartridge,
wherein the plurality of legs define rails and comprise at least a first leg, a second leg, a third leg, and a fourth leg,
wherein the cartridge includes a bottom wall, a sidewall that extends from the bottom wall, and a flange extending away from the sidewall,
wherein the cartridge is nested within the receptacle and is held in place with retaining features that include the plurality of legs,
wherein the impermeable membrane prevents volatile from escaping from the cartridge until air from a surrounding environment is allowed to enter into the reservoir,
wherein the first leg and the second leg are disposed on a first side of the central plane, and the third leg and the fourth leg are disposed on a second side of the central plane, opposite the first side, and
wherein distal ends of the first leg, the second leg, the third leg, and the fourth leg are in direct contact with the flange when the dispenser is in an activated configuration.

20. The dispenser of claim 19, wherein the flange extends outward from an upper end of the sidewall.

21. The dispenser of claim 19, wherein the plurality of apertures allow air to flow into a bottom portion of the housing, which is coupled with a top portion of the housing, the housing being configured to be moved between an open configuration and a closed configuration.

* * * * *